(12) United States Patent
Couture-Dorschner et al.

(10) Patent No.: US 7,156,833 B2
(45) Date of Patent: Jan. 2, 2007

(54) ABSORBENT ARTICLE WITH FASTENING SYSTEM

(75) Inventors: Laurie Couture-Dorschner, Hortonville, WI (US); Heather Schenck Mortell, Neenah, WI (US); David Arthur Kuen, Neenah, WI (US); Robert Lee Popp, Hortonville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 373 days.

(21) Appl. No.: 10/023,457

(22) Filed: Dec. 17, 2001

(65) Prior Publication Data

US 2003/0125702 A1    Jul. 3, 2003

(51) Int. Cl.
*A61F 13/15*    (2006.01)

(52) U.S. Cl. ............. 604/387; 604/385.03; 604/391; 604/394

(58) Field of Classification Search .............. 604/396, 604/387, 389, 391, 385.24, 385.31, 386, 604/394, 392, 385.03
See application file for complete search history.

(56) References Cited

U.S. PATENT DOCUMENTS

| 4,145,763 | A | 3/1979 | Abrams et al. ............. 2/403 |
| 4,205,679 | A | 6/1980 | Repke et al. .............. 128/287 |
| 4,317,449 | A | 3/1982 | Nowakoski |
| 4,402,690 | A | 9/1983 | Redfern .................... 604/391 |
| 4,610,680 | A | 9/1986 | LaFleur ................ 604/385 A |
| 4,615,695 | A | 10/1986 | Cooper ................. 604/385 A |
| 4,619,649 | A | 10/1986 | Roberts |
| 4,630,320 | A | 12/1986 | Van Gompel |
| 4,663,220 | A | 5/1987 | Wisneski et al. |
| 4,699,622 | A | 10/1987 | Toussant et al. ........... 604/389 |
| 4,940,464 | A | 7/1990 | Van Gompel et al. |
| 5,046,272 | A | 9/1991 | Vogt et al. |
| 5,087,253 | A | 2/1992 | Cooper ................... 604/385.1 |
| 5,104,116 | A | 4/1992 | Pohjola |
| 5,224,405 | A | 7/1993 | Pohjola |
| 5,226,992 | A | 7/1993 | Morman |
| 5,370,634 | A | 12/1994 | Ando et al. |
| 5,624,428 | A | * | 4/1997 | Sauer ..................... 604/391 |
| 5,662,638 | A | 9/1997 | Johnson et al. |
| 5,779,831 | A | 7/1998 | Schmitz .................. 156/73.1 |
| 5,785,699 | A | 7/1998 | Schmitz .................. 604/391 |
| 5,795,350 | A | 8/1998 | Schmitz .................. 604/391 |
| 5,830,206 | A | 11/1998 | Larsson .................. 604/390 |
| 5,855,574 | A | 1/1999 | Kling et al. |
| 5,897,545 | A | 4/1999 | Kline et al. ............. 604/386 |
| 6,113,717 | A | 9/2000 | Vogt et al. |
| 6,287,287 | B1 | 9/2001 | Elsberg |
| 6,328,725 | B1 | 12/2001 | Fernfors ................. 604/391 |
| 6,395,115 | B1 | 5/2002 | Popp et al. ............... 156/66 |
| 6,409,858 | B1 | 6/2002 | Popp et al. ............... 156/66 |

(Continued)

FOREIGN PATENT DOCUMENTS

EP    217 032    2/1992

(Continued)

*Primary Examiner*—Jacqueline Stephens
(74) *Attorney, Agent, or Firm*—Pauley Petersen & Erickson

(57) ABSTRACT

A pant-like absorbent refastenable garment adapted to easy application and removal has hook and loop fasteners on the front and back side panels and in particular embodiments frangible bonds connecting the front and back side panels. The frangible bonds connecting the front and back side panels can be easily broken by the user prior to use and the hook and loop fasteners can be engaged prior to, or during, donning. The hook and loop fasteners do not need to be prefastened at the time of manufacture.

43 Claims, 19 Drawing Sheets

U.S. PATENT DOCUMENTS

| | | | |
|---|---|---|---|
| 6,432,243 B1 | 8/2002 | Popp et al. | 156/204 |
| 6,432,248 B1 | 8/2002 | Popp et al. | 156/256 |
| 6,447,628 B1 | 9/2002 | Couillard et al. | 156/204 |
| 6,461,344 B1 | 10/2002 | Widlund et al. | 604/390 |
| 6,481,362 B1 | 11/2002 | Hietpas et al. | 112/475.06 |
| 6,497,032 B1 | 12/2002 | Maxton et al. | 29/429 |
| 6,513,221 B1 | 2/2003 | Vogt et al. | 29/429 |
| 6,514,187 B1 | 2/2003 | Coenen et al. | 493/418 |

FOREIGN PATENT DOCUMENTS

| | | |
|---|---|---|
| EP | 0 757 550 B1 | 12/1998 |
| GB | 1 520 740 | 8/1978 |
| GB | 2 267 024 A | 11/1993 |
| JP | 4-117618 | 10/1992 |
| WO | 95/27460 | 10/1995 |
| WO | 95/27462 | 10/1995 |
| WO | WO 95/29657 | 11/1995 |
| WO | 97/23180 | 7/1997 |
| WO | WO 99/65441 | 12/1999 |
| WO | WO 00/23025 | 4/2000 |
| WO | 00/35396 | 6/2000 |
| WO | 00/35398 | 6/2000 |
| WO | 00/37009 | 6/2000 |
| WO | 01/13844 | 3/2001 |
| WO | 01/13845 | 3/2001 |
| WO | 01/13846 | 3/2001 |
| WO | 01/13847 | 3/2001 |
| WO | 01/13848 | 3/2001 |
| WO | 01/13850 | 3/2001 |

\* cited by examiner

ABSORBENT ARTICLE WITH FASTENING SYSTEM

BACKGROUND OF THE INVENTION

This invention is directed to a fastenable or refastenable personal care garment having fasteners on the side panels for ease of removal and donning without complete removal of a wearer's clothing.

Garments with refastenable sides are commonly manufactured so that the fastening components are engaged or prefastened at manufacture. Engaging the fastening component and mating fastening component can involve folding and manipulating the garment, and such folding and manipulating can be difficult and time consuming to accomplish. Garments with refastenable sides can also be prone to poor fastener performance if the side panels are misaligned or tucked into the product in such a way as to cause creasing of a resilient fastening component.

When the refastenable sides include a resilient fastening component such as a hook component, these creases can deaden the hooks, thereby reducing the engageable area. As a result, a creased fastener tends to possess lower peel and/or shear values than uncreased fasteners. Products with severe and/or multiple fastener creases tend to be most apt to pop open during application and wear. Fastener creases appear to be more of an issue for hook components than for loop components due to the possibility of permanent deformation of hook material compared to the relative flexibility of loop material. One potential source of these performance-impairing creases may be the orientation of the panel bearing the resilient fastening component after tucking of the panel and during product compression for packaging.

There is a need or desire to reduce both material and manufacturing costs associated with garments without sacrificing performance and quality. However, this should be accomplished without compromising the performance characteristics of the various regions in the garment.

There is also a need or desire for pant-like, personal care absorbent garments that can be easily and reliably pulled on over a wear's legs and hips.

SUMMARY OF THE INVENTION

In response to the discussed difficulties, this invention is directed in particular embodiments to a fastenable or refastenable personal care garment, including a low strength frangible bond connecting the front side panels and the back side panels, for which the fastening system does not need to be prefastened at the time of manufacture. The side panels can, therefore, be manufactured flat against each other and not overlapped for the purpose of engaging the fasteners. The frangible bond can be easily broken by the user prior to use and the fasteners can be engaged prior to, or during, donning.

The strength of the bond connecting the side panels should be at a maximum 3000 grams measured by the Bond Strength Test Procedure. These low strength bonds are frangible, meaning that they are intended to be easily broken by the consumer. The low strength bonds can run either a partial length or a full length of the side panels. The consumer first breaks the frangible bonds, then dons the product by first prefastening the fasteners, or in the alternative the consumer could don the product with the fasteners unfastened and the frangible bond intact.

In one embodiment of the invention, a frangible bond can attach each front side panel to each back side panel with the frangible bond located between the fastening component and the distal edge of the front side panel and between the mating fastening component and the distal edge of the back side panel. In other alternative embodiments, the frangible bond can be located inward of the fastening component and the mating fastening component, or through the fastening component and the mating fastening component.

In another embodiment of the invention, the frangible bond can be located on a tab which extends from the distal edge of each side panel. The tabs can be located either adjacent the waist opening of the garment or mid-way down the side of the garment or at the leg opening.

In still another embodiment, either the front side panel or the back side panel can include an attachment surface and the other of the front side panel or back side panel can include a mating fastening component. The attachment surface can be releasably engageable with the fastening component. In alternative embodiments, the location of the frangible bond can vary from between the fastening component and the distal edge of the side panel, inward from the fastening component or directly through the fastening component.

In still another embodiment, the side panel including an attachment surface can additionally include a perforation. The perforation can be located either inward or outward of the frangible bond. The perforation can be broken by the consumer and the broken end of the perforation can be inserted between the inner surfaces of the front and back side panels and the distal edges.

In still another embodiment of the invention, the front or back side panels can include an attachment surface and the other of the front side panel or the back side panel can include a fastening component on the inner surface. The front side panels and back side panels are not bonded together in this embodiment and also do not include perforations. However, the inside surfaces of the front side panel and the back side panel face, and lie flat upon, each other and the attachment surface engages the fastening component so that no folding or manipulating of the side panels is required during manufacturing.

With the foregoing in mind, it is a feature and advantage of the invention to provide a fastenable or refastenable garment that does not require that the fastening system be prefastened at the time of manufacture.

It is also a feature and advantage of particular embodiments of the invention to provide a pant-like absorbent refastenable garment with frangible bonds connecting the side panels.

It is also a feature and advantage of particular embodiments of the invention to provide a pant-like absorbent refastenable garment with frangible bonds connecting the side panels and perforations in the side panels.

It is also a feature and advantage of the invention to provide a pant-like absorbent refastenable garment in which the side panels do not require folding or manipulation during manufacture.

DEFINITIONS

Figure 1A:
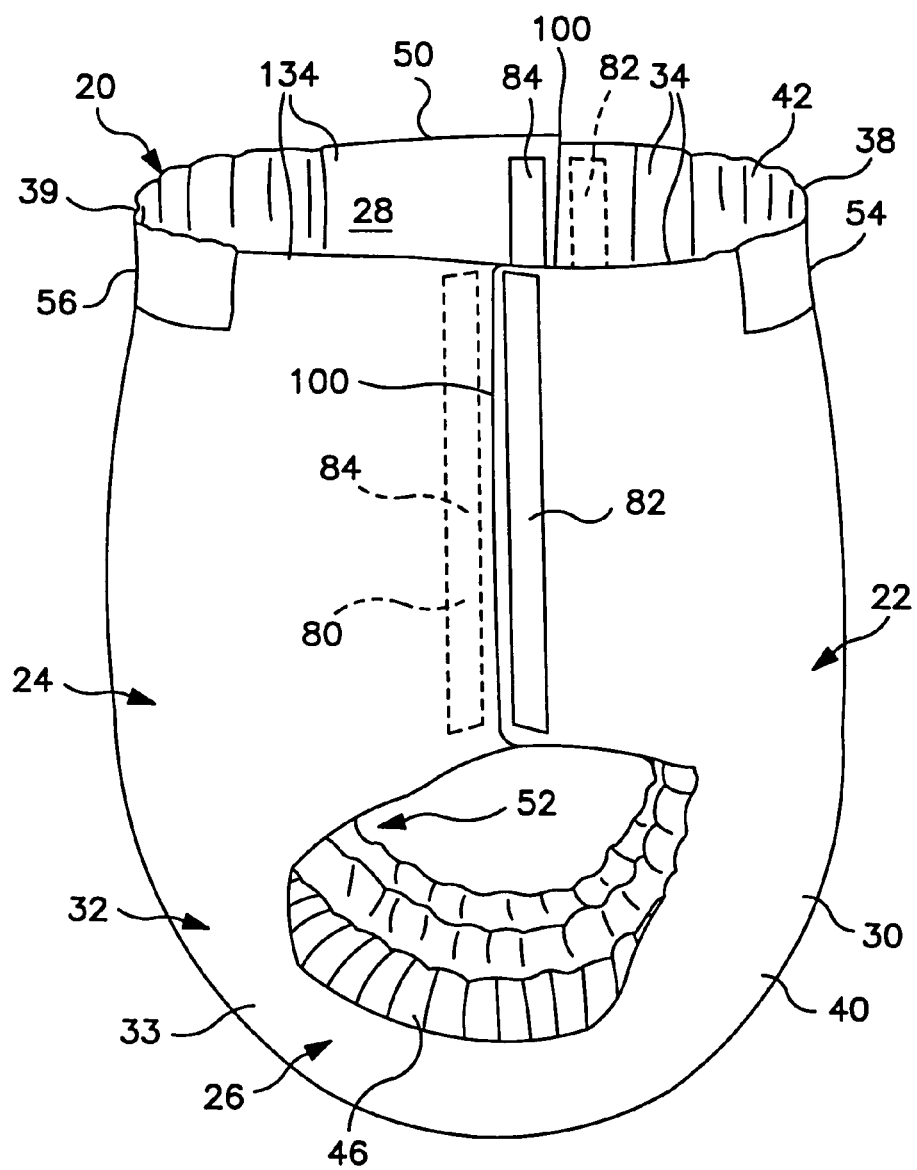
FIG. 1A is a side perspective view of an absorbent refastenable garment having a frangible bond connecting a front side panel and a back side panel, showing a fastening component on an outer surface of the front side panel and a mating fastening component on an inner surface of the back side panel.

Within the context of this specification, each term or phrase below will include the following meaning or meanings.

"Bond," when used in the singular can have the dual meaning of a single bond point or a plurality of bond points. The shapes of the plurality of bond points can, but need not be, uniform.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Connected" refers to the joining, adhering, bonding, attaching, or the like, of two elements. Two elements will be considered to be connected together when they are connected directly to one another or indirectly to one another, such as when each is directly connected to intermediate elements.

"Cross direction" refers to the width of a fabric in a direction generally perpendicular to the direction in which it is produced, as opposed to "machine direction" which refers to the length of a fabric in the direction in which it is produced.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Fastening component" refers to a hook or loop fastener as known in the art, but can also include other components used to fasten such as, adhesives, cohesives, snaps, buttons and the like. "Fastening component," when used in the singular, can also include multiple components.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

"Flexible" refers to materials which are compliant and which will readily conform to the general shape and contours of the wearer's body.

"Frangible bond" refers to a nonrefastenable bond designed and intended to be separated one time by the user, when desired. The frangible bond comes apart without substantially destroying or deforming the functional properties or characteristics of the materials that are bonded together. The frangible bond can be effectuated via ultrasonic welding, thermal bonding, crimping, cohesives, adhesives, compression, nipping, needle punching, sewing, hydroentangling, and similar technologies known in the art.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

"Integral" or "integrally" is used to refer to various portions of a single unitary element rather than separate structures bonded to or placed with or placed near one another.

"Inward" and "outward" refer to positions in the transverse direction relative to the longitudinal center line of the training pant, and particularly closer to, or away from, the longitudinal center line, respectively.

"Layer" when used in the singular can have the dual meaning of a single element or a plurality of elements.

"Liquid impermeable," when used in describing a layer or multi-layer laminate means that liquid, such as urine, will not pass through the layer or laminate under ordinary use conditions in a direction generally perpendicular to the plane of the layer or laminate at the point of liquid contact.

"Liquid permeable material" refers to a layer or laminate that is not liquid impermeable.

Figure 2:
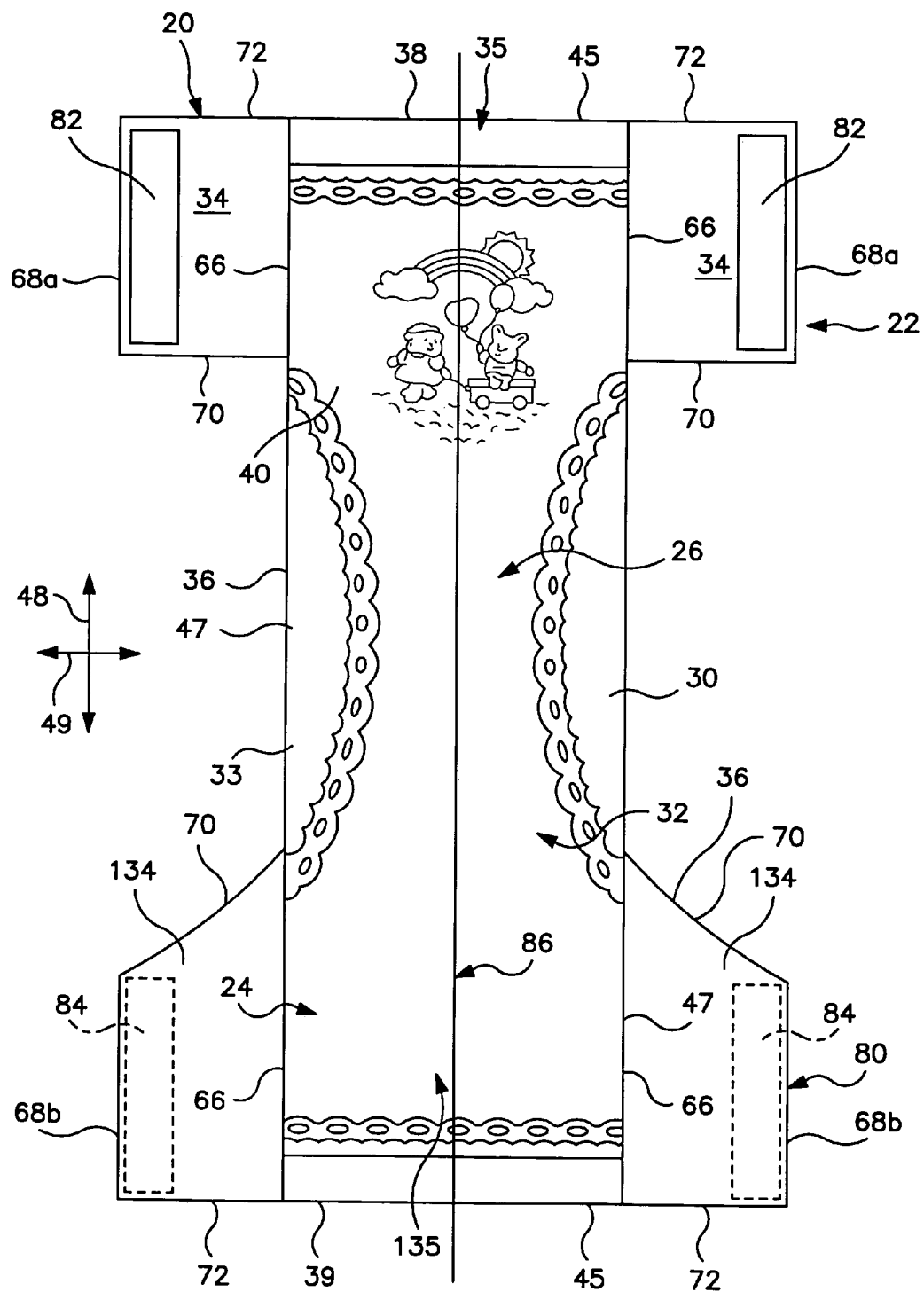
FIG. 2 is a plan view of the absorbent garment of FIG. 1A in a partially disassembled, stretched flat state, and showing the surface of the article that faces away from the wearer when the article is worn.
Figure 3:
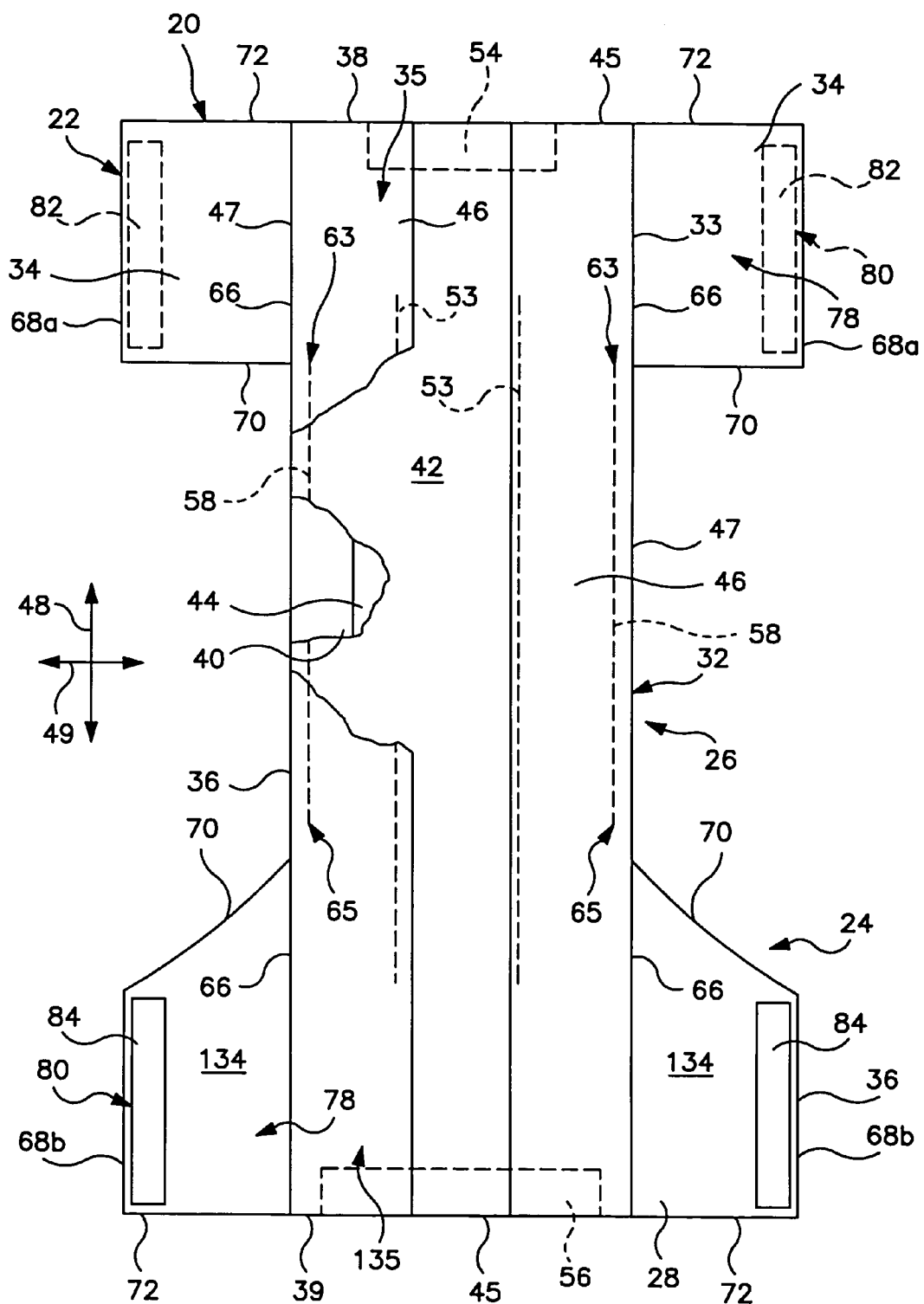
FIG. 3 is a plan view of the absorbent garment of FIG. 1A in a partially disassembled, stretched flat state, and showing the surface of the article that faces the wearer when the article is worn, and with portions cut away to show the underlying features.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Machine direction" refers to the length of a fabric in the direction in which it is produced, as opposed to "cross direction" which refers to the width of a fabric in a direction generally perpendicular to the machine direction.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," in reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Perforation" refers to any form of cut or cuts or line of weakness necessary to achieve the separability of the material into separate parts prior to, or upon, use by the wearer.

"Permanently bonded" refers to the joining, adhering, connecting, attaching, or the like, of two elements of an absorbent garment such that the elements tend to be and remain bonded during normal use conditions of the absorbent garment.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Rupture" means the breaking or tearing apart of a material; in tensile testing, the term refers to the total separation of a material into two parts either all at once or in stages, or the development of a hole in some materials.

"Spunbonded fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, to at least 150% of its initial (unstretched) length in at least one direction, suitably to at least 200% of its initial length, desirably to at least 250% of its initial length.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Tension" includes a uniaxial force tending to cause the extension of a body or the balancing force within that body resisting the extension.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE PRESENTLY PREFERRED EMBODIMENTS

The present invention is directed in particular embodiments to a pant-like absorbent garment having refastenable fasteners, such as hook and loop fasteners, on the side panels for ease of removal and donning of the absorbent garment without complete removal of a wearer's clothing, and also having frangible bonds connecting the front and back side panels.

The principles of the present invention can be incorporated into any suitable disposable absorbent article. Examples of such suitable articles include diapers, training pants, feminine hygiene products, incontinence products, other personal care or health care garments, or the like. For ease of explanation, the description hereafter will be in terms of a child's training pant.

Figure 1B:
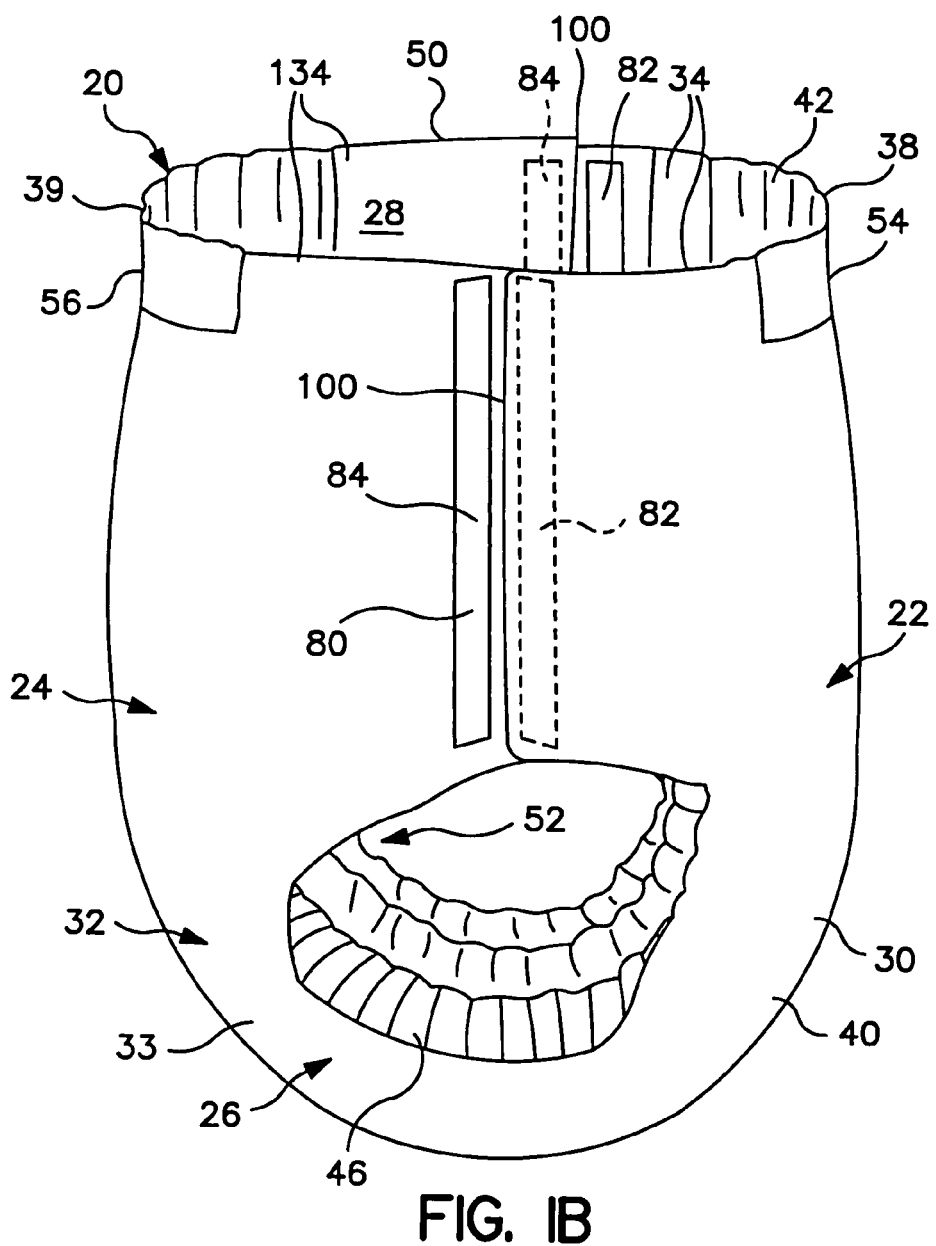
FIG. 1B is a side perspective view of an absorbent refastenable garment having a frangible bond connecting a front side panel and a back side panel, showing a fastening component on an inner surface of the front side panel and a mating fastening component on an outer surface of the back side panel.

Referring to FIGS. 1A and 1B, a disposable absorbent article, such as a training pant 20, is illustrated. The training pant 20 includes an absorbent chassis 32 and a fastening system 80. The absorbent chassis 32 defines a front region 22, a back region 24, a crotch region 26 interconnecting the front and back regions, an inner surface 28 which is configured to contact the wearer, and an outer surface 30 opposite the inner surface which is configured to contact the wearer's clothing. With additional reference to FIGS. 2 and 3, the absorbent chassis 32 also defines a pair of transversely opposed side edges 36 and a pair of longitudinally opposed waist edges, which are designated front waist edge 38 and back waist edge 39. The front region 22 is contiguous with the front waist edge 38, and the back region 24 is contiguous with the back waist edge 39.

The illustrated absorbent chassis 32 includes a somewhat rectangular composite structure 33, a pair of transversely opposed front side panels 34, and a pair of transversely opposed back side panels 134. The composite structure 33 and side panels 34 and 134 can be integrally formed, as shown in FIGS. 1A and 1B, or can include two or more separate elements, as shown in FIGS. 2 and 3. The illustrated composite structure 33 includes an outer cover 40, a bodyside liner 42 which is connected to the outer cover in a superposed relation, an absorbent assembly 44 (FIG. 3) which is located between the outer cover 40 and the bodyside liner 42, and a pair of containment flaps 46 (FIG. 3). The somewhat rectangular composite structure 33 has opposite linear end edges 45 that form portions of the front and back waist edges 38 and 39, and opposite linear or curvilinear side edges 47 that form portions of the side edges 36 of the absorbent chassis 32 (FIGS. 2 and 3). For reference, arrows 48 and 49 depicting the orientation of the longitudinal axis and the transverse axis, respectively, of the training pant 20 are illustrated in FIGS. 2 and 3.

In the training pant 20 as illustrated in FIGS. 1A and 1B, the front and back regions 22 and 24 are joined together to define a three-dimensional pant configuration having a waist opening 50 and a pair of leg openings 52. The front region 22 includes the portion of the training pant 20 which, when worn, is positioned on the front of the wearer while the back region 24 includes the portion of the training pant which, when worn, is positioned on the back of the wearer. The crotch region 26 of the training pant 20 includes the portion of the training pant which, when worn, is positioned between the legs of the wearer and covers the lower torso of the wearer. The front and back side panels 34 and 134 include the portions of the training pant 20 which, when worn, are positioned on the hips of the wearer.

The front region 22 of the absorbent chassis 32 includes the transversely opposed front side panels 34 and a front center panel 35 (FIGS. 2 and 3) positioned between and interconnecting the front side panels 34, along with a front waist elastic member 54 (FIG. 3) and any other connected components. The back region 24 of the absorbent chassis 32 includes the transversely opposed back side panels 134 and a back center panel 135 (FIGS. 2 and 3) positioned between and interconnecting the side panels, as well as a rear waist elastic member 56 (FIG. 3) and any other connected components. The waist edges 38 and 39 of the absorbent chassis 32 are configured to encircle the waist of the wearer when worn and provide the waist opening 50 which defines a waist perimeter dimension. Portions of the transversely opposed side edges 36 in the crotch region 26 generally define the leg openings 52.

The absorbent chassis 32 is configured to contain and/or absorb any body exudates discharged from the wearer. For example, the absorbent chassis 32 can include the pair of containment flaps 46 which are configured to provide a barrier to the transverse flow of body exudates. A flap elastic member 53 (FIG. 3) is operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed side edges of the absorbent chassis 32, and can extend longitudinally along the entire length of the absorbent chassis or can only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 can include the front waist elastic member 54, the rear waist elastic member 56, and leg elastic members 58, as are known to those skilled in the art (FIG. 3). The waist elastic members 54 and 56 can be operatively joined to the outer cover 40 and/or bodyside liner 42 along the opposite waist edges 38 and 39, and can extend over part or all of the waist edges. The leg elastic members 58 can be operatively joined to the outer cover 40 and/or bodyside liner 42 along the opposite side edges 36 and positioned in the crotch region 26 of the training pant 20. The leg elastic members 58 can be longitudinally aligned along each side edge 47 of the composite structure 33. Each leg elastic member 58 has a front terminal point 63 and a back terminal point 65, which points represent the longitudinal ends of the elastic gathering caused by the leg elastic members. The front terminal points 63 can be located adjacent the longitudinally innermost parts of the front side panels 34, and the back terminal points 65 can be located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic constrictive forces are imparted to the substrate. In one particular embodiment, for example, the leg elastic members 58 include a plurality of dry-spun coalesced multifilament spandex elastomeric threads sold under the trade name LYCRA® and available from E.I. DuPont de Nemours and Company, Wilmington, Del., U.S.A.

The outer cover 40 can include a material that is substantially liquid impermeable, and can be elastic, stretchable or nonstretchable. The outer cover 40 can be a single layer of liquid impermeable material, but can include a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and can be one that provides a generally cloth-like texture. One example of such a material is a 20 gsm (grams per square meter) spunbond polypropylene nonwoven web. The outer layer can also be made of those materials of which liquid permeable bodyside liner 42 is made. While it is not a necessity for the outer layer to be liquid permeable, it can provide a relatively cloth-like texture to the wearer.

The inner layer of the outer cover 40 can be both liquid and vapor impermeable, or can be liquid impermeable and vapor permeable. The inner layer can be manufactured from a thin plastic film, although other flexible liquid impermeable materials can also be used. The inner layer, or the liquid impermeable outer cover 40 when a single layer, prevents waste material from wetting articles, such as bedsheets and clothing, as well as the wearer and care giver. A suitable liquid impermeable film for use as a liquid impermeable inner layer, or a single layer liquid impermeable outer cover 40, is a 0.2 millimeter polyethylene film commercially available from Huntsman Packaging of Newport News, Va., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

The liquid permeable bodyside liner 42 is illustrated as overlying the outer cover 40 and absorbent assembly 44 (FIG. 3), and can but need not have the same dimensions as the outer cover 40. The bodyside liner 42 can be compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL® N-62 from Uniqema Inc., a division of ICI of New Castle, Del., U.S.A. and GLUCOPON® 220UP available from Cognis Corporation of Ambler, Pa., and produced in Cincinnati, Ohio, in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal center line 86.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and bodyside liner 42 can include elastomeric materials, in some embodiments the composite structure can be generally inelastic, where the outer cover, the bodyside liner and the absorbent assembly include materials that are generally not elastomeric.

The absorbent assembly 44 (FIG. 3) is positioned between the outer cover 40 and the bodyside liner 42, which components can be joined together by any suitable means, such as adhesives, as is well known in the art. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably include a matrix of hydrophilic fibers, such as a web of cellulosic fluff, mixed with particles of a high-absorbency material commonly known as superabsorbent material. In a particular embodiment, the absorbent assembly 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be non-uniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and can be capable of absorbing more than about 25 times its weight in water.

In one embodiment, the absorbent assembly 44 is generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly 44 in an amount of from about 0 to about 90 weight percent based on total weight of the absorbent assembly. The absorbent assembly 44 suitably has a density within the range of about 0.10 to about 0.50 grams per cubic centimeter. The absorbent assembly 44 can be wrapped or encompassed by a suitable tissue wrap that maintains the integrity and/or shape of the absorbent assembly.

The absorbent chassis 32 can also incorporate other materials that are designed primarily to receive, temporarily store, and/or transport liquid along the mutually facing surface with the absorbent assembly 44, thereby maximizing the absorbent capacity of the absorbent assembly. One suitable material is referred to as a surge layer (not shown) and includes a material having a basis weight of about 50 to about 120 grams per square meter, and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C., U.S.A.

As noted previously, the illustrated training pant 20 has front and back side panels 34 and 134 disposed on each side of the absorbent chassis 32. The front side panels 34 form part of the front region 22. The back side panels form part of the back region. Each of the front side panels 34 and each of the back side panels 134 have an inner surface and an outer surface corresponding to the inner surface 28 and the outer surface 30 of the chassis 32. These transversely opposed front side panels 34 and transversely opposed back side panels 134 can be permanently bonded to the composite structure 33 of the absorbent chassis 32 in the respective front and back regions 22 and 24, and can be releasably attached to one another by a fastening system 80. More particularly, as shown best in FIGS. 2 and 3, the front side panels 34 can be permanently bonded to and extend transversely beyond the linear or curvilinear side edges 47 of the composite structure 33 in the front region 22 along attachment lines 66, and the back side panels 134 can be permanently bonded to and extend transversely beyond the linear or curvilinear side edges 47 of the composite structure 33 in the back region 24 along attachment lines 66. The side panels 34 and 134 can be attached using attachment means known to those skilled in the art such as adhesive, thermal or ultrasonic bonding. The side panels 34 and 134 can also be formed as a portion of a component of the composite structure 33, such as the outer cover 40 or the bodyside liner 42, as shown in FIGS. 1A and 1B.

In particular embodiments for improved fit and appearance, the side panels 34 and 134 can have an average length dimension measured parallel to the longitudinal axis 48 that is about 20 percent or greater, and particularly about 26 percent or greater, of the overall length dimension of the absorbent article, also measured parallel to the longitudinal axis 48. For example, in training pants having an overall length dimension of about 52 centimeters, the side panels 34 and 134 can each have an average length dimension of about 10 centimeters or greater, such as about 14 centimeters. While each of the side panels 34 and 134 extend from the waist opening 50 to one of the leg openings 52, the back side panels 134 have a decreasing length dimension moving from the attachment line 66 to a distal edge 68b of the back panel 134, as is best shown in FIGS. 2 and 3.

Each of the side panels 34 and 134 can include one or more individual, distinct pieces of material. In particular embodiments, for example, each side panel 34 and 134 can include first and second side panel portions that are joined at a seam, with at least one of the portions including an elastomeric material. Still alternatively, each individual side panel 34 and 134 can include a single piece of material which is folded over upon itself along an intermediate fold line (not shown).

The side panels 34 and 134 can include an elastic material capable of stretching in a direction generally parallel to the transverse axis 49 of the training pant 20. In particular embodiments, the front and back side panels 34 and 134 can each include an interior portion 78 (FIG. 3) disposed between the distal edge 68a, 68b and the respective front or back center panel 35 or 135. In the illustrated embodiment in FIG. 3, the interior portions 78 are disposed between the distal edges 68a, 68b and the side edges 47 of the somewhat rectangular composite structure 33. The elastic material of the side panels 34 and 134 can be disposed in the interior portions 78 to render the side panels elastomeric in a direction generally parallel to the transverse axis 49. Alternatively, each side panel 34 and 134 is elastomeric from a waist end edge 72 to a leg end edge 70. More specifically, individual samples of side panel material, taken between the waist end edge 72 and the leg end edge 70 parallel to the transverse axis 49 and having a length from the attachment line 66 to the distal edge 68a, 68b and a width of about 2 centimeters, are all elastomeric.

Suitable elastic materials, as well as one described process of incorporating elastic side panels into a training pant, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material includes a stretch-thermal laminate (STL), a neck-bonded laminated (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material can include other woven or nonwoven materials, such as those described above as being suitable for the outer cover 40 or bodyside liner 42, or stretchable but inelastic materials.

The training pant 20 according to the present invention also includes a fastening system 80 for securing the training pant about the waist of the wearer (FIGS. 1A and 1B). The illustrated fastening system 80 includes fastening components 82 that are adapted to refastenably connect to mating fastening components 84. In one embodiment, one surface of each of the fastening components 82 and 84 includes a plurality of engaging elements that project from that surface. The engaging elements of these fastening components 82 are adapted to repeatedly engage and disengage the engaging elements of the mating fastening components 84.

The fastening components 82 can be located on the outer surface of the front side panels 34 and the mating fastening components 84 can be located on the inner surface of the back side panels 134, as shown in FIGS. 1A, 2 and 3. (The dotted lines indicate that the fastening component 82 or the mating fastening component 84 is located on the opposite surface visible in the drawing.) Alternatively, as shown in FIG. 1B, the fastening components 82 can be located on the inner surface of the front side panels 34, and the mating fastening components 84 can be located on the outer surface of the back side panels 134.

In one particular embodiment, the fastening components 82 each include hook type fasteners and the mating fastening components 84 each include complementary loop type fasteners. In another particular embodiment, the fastening components 82 each include loop type fasteners and the mating fastening components 84 each include complementary hook type fasteners. The fastening components 82 and the mating fastening components 84 can be rectangular, although they can alternatively be square, round, oval, curved or otherwise non-rectangularly shaped.

Loop type fasteners typically include a fabric or material having a base or backing structure and a plurality of loop members extending upwardly from at least one surface of the backing structure. The loop material can be formed of any suitable material, such as acrylic, nylon or polyester, and can be formed by methods such as warp knitting, stitch bonding or needle punching. Suitable loop materials are available from Guilford Mills, Inc., Greensboro, N.C., U.S.A. under the trade designation No. 36549.

Hook type fasteners typically include a fabric or material having a base or backing structure and a plurality of hook members extending upwardly from at least one surface of the backing structure. In contrast to the loop type fasteners which include a flexible fabric, the hook material advantageously includes a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. Suitable single-sided hook materials for the fastening components 82 or the mating fastening components 84 are available from Velcro Industries B.V., Amsterdam, Netherlands or affiliates thereof, and are identified as Velcro HTH-829 with a unidirectional hook pattern and having a thickness of about 0.089 millimeters (3.5 mils) and HTH-851 with a unidirectional hook pattern and having a thickness of about 0.051 millimeters (2 mils).

Figure 4:
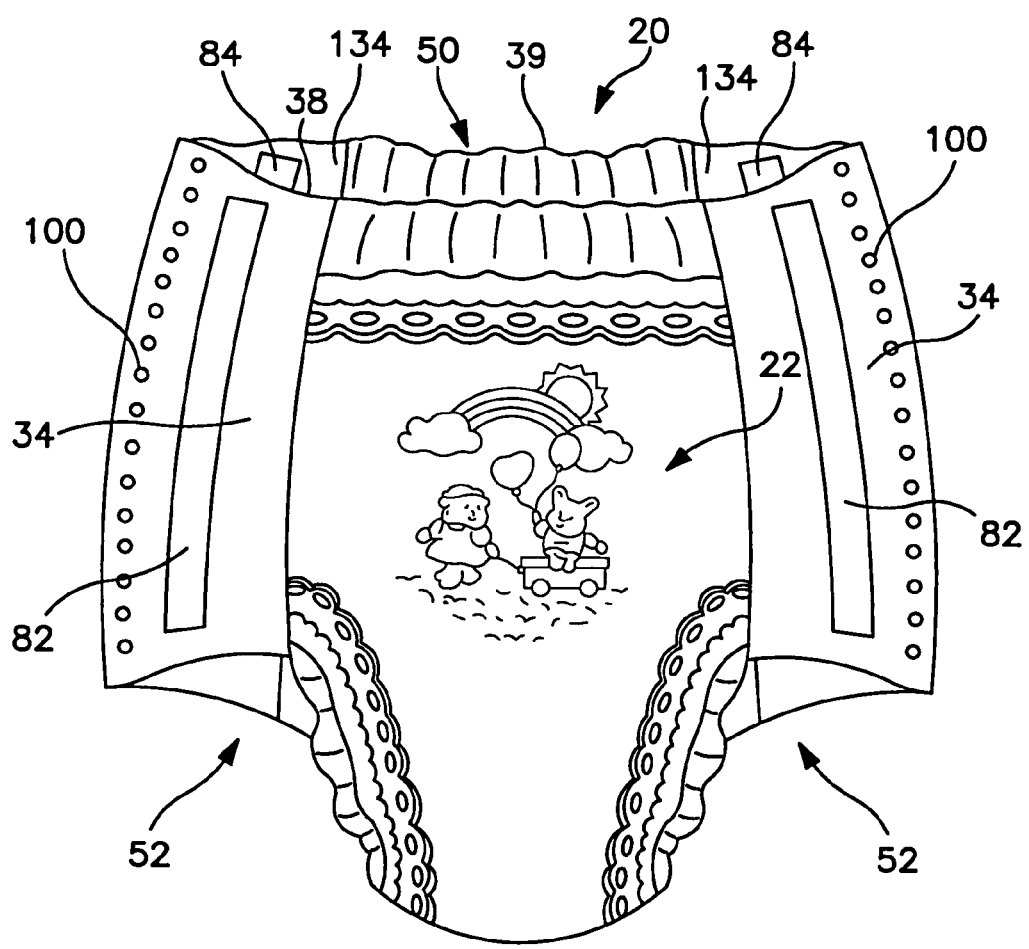
FIG. 4 is a front view of the absorbent garment of FIG. 1A showing a frangible bond connecting the front side panel and the back side panel.

In particular embodiments of the invention, the training pant 20 further includes a frangible bond 100 connecting each front side panel 34 and each back side panel 134 (FIGS. 1A, 1B and 4). The manufacture of training pants with fastening components can be accomplished in the manner described in U.S. patent application Ser. No. 09/855,484 filed May 15, 2001 by Joseph D. Coenen et al., which is incorporated herein by reference. The same process described therein, absent the steps involved for engaging the fastening components 82 to the mating fastening components 84, can be used to manufacture the training pants of the present invention. The provision of frangible bonds 100 can be accomplished in the manner described in U.S. Pat. No. 5,046,272, issued Sep. 10, 1991 to Vogt et al., which is incorporated herein by reference.

The refastenable training pant 20 of the embodiment shown in FIG. 1A is an absorbent product having refastenable hook and loop fasteners, 82 and 84, respectively, and frangible bonds 100. As is known in the art for bonding side panels together, the frangible bond 100 can be oriented as a "lap seam" or a "butt seam," along the distal edges 68a and 68b of the front and back side panels 34 and 134. The term "lap seam," as used herein, refers to a seam connecting the front and back side panels 34 and 134 such that the front and back side panels and/or materials bonded thereto overlap. The term "butt seam," as used herein, refers to a seam connecting the front and back side panels 34 and 134 such that the inner surface of the front and back side panels 34 and 134 face each other. Whether the frangible bonds 100 are oriented as lap seams or butt seams, each frangible bond 100 connects a front side panel 34 to a back side panel 134. When the frangible bonds 100 are oriented as butt seams, the inner surface of each front side panel 34 and the inner surface of each back side panel 134 face each other, and the front side panels 34 and back side panels 134 can lie in a flat position. When the frangible bonds 100 are oriented as lap seams, the portions of each front side panel 34 and each back side panel 134 which are connected by the frangible bond 100 overlap. However, the inner surface of the remainder of each front side panel 34 and the inner surface of the remainder of each back side panel 134 face each other, and can lie in a flat position.

Referring to FIG. 1A, the absorbent chassis 32 and the frangible bonds 100 together define a refastenable training pant 20 having a waist opening 50 and a pair of leg openings 52. The fastening components 82 and the mating fastening components 84 are in the unfastened condition, and are engageable only upon breaking the frangible bonds 100. As mentioned previously, the consumer has the option of first breaking the frangible bonds 100, then donning the training pant 20 by first prefastening the fastening components 82 and mating fastening components 84, or in the alternative the consumer could don the product with frangible bonds 100 intact and the fastening components 82 and mating fastening components 84 unfastened. The refastenable product includes a pair of front side panels 34 extending from the waist opening 50 to each leg opening 52, a pair of elastomeric back side panels 134 extending from the waist opening 50 to each leg opening 52, an elastomeric front waistband 54 disposed on the front side 22 and positioned between the pair of elastomeric front side panels 34, an elastomeric back waistband 56 disposed on the back side 24 and positioned between the pair of elastomeric back side panels 134, and at least a pair of the leg elastic members 58 which partially encircle each leg opening 52. More than one leg elastic member 58 can partially or fully encircle each leg opening 52. Each leg elastic member 58 extends from adjacent an elastomeric front side panel 34 on the front side 22 to adjacent an elastomeric back side panel 134 on the back side 24.

Figure 6:
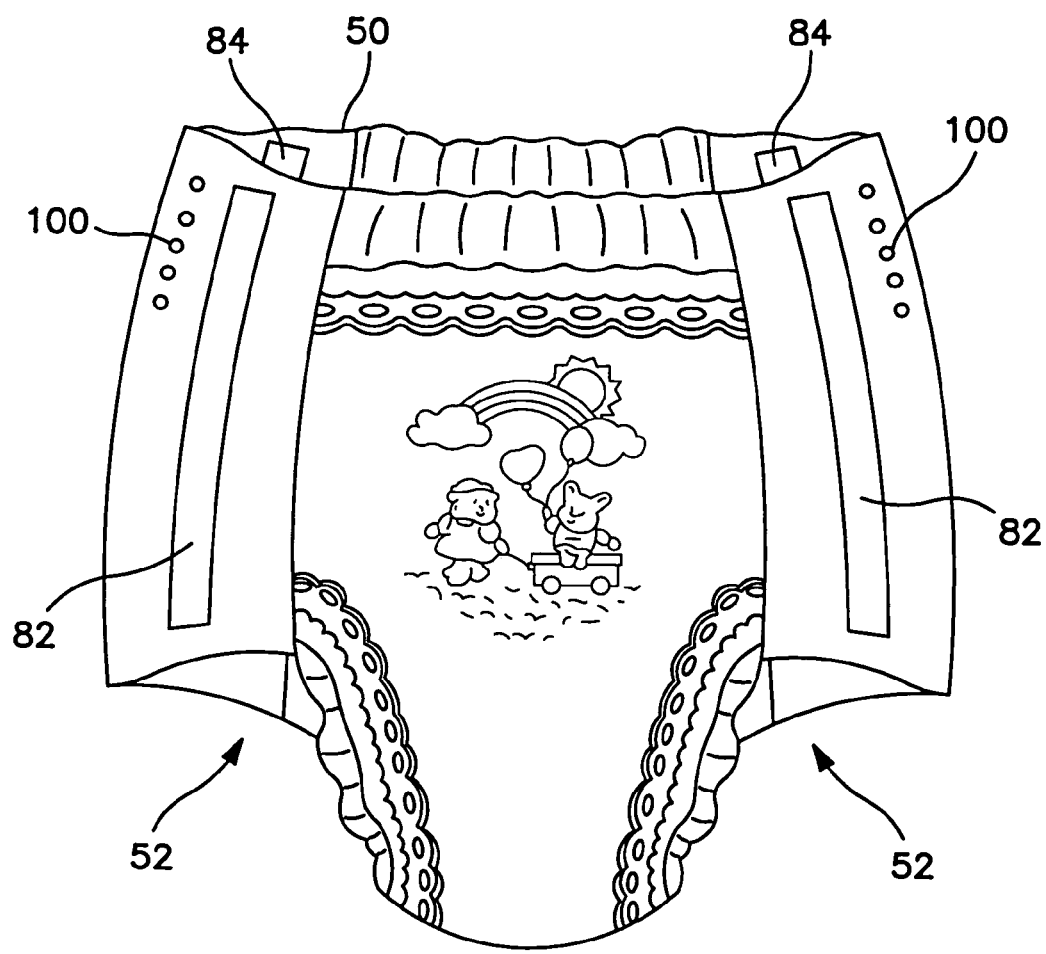
FIG. 6 is a front view of an absorbent garment showing a partial length frangible bond adjacent the waist opening connecting the front side panels and the back side panels.
Figure 7:
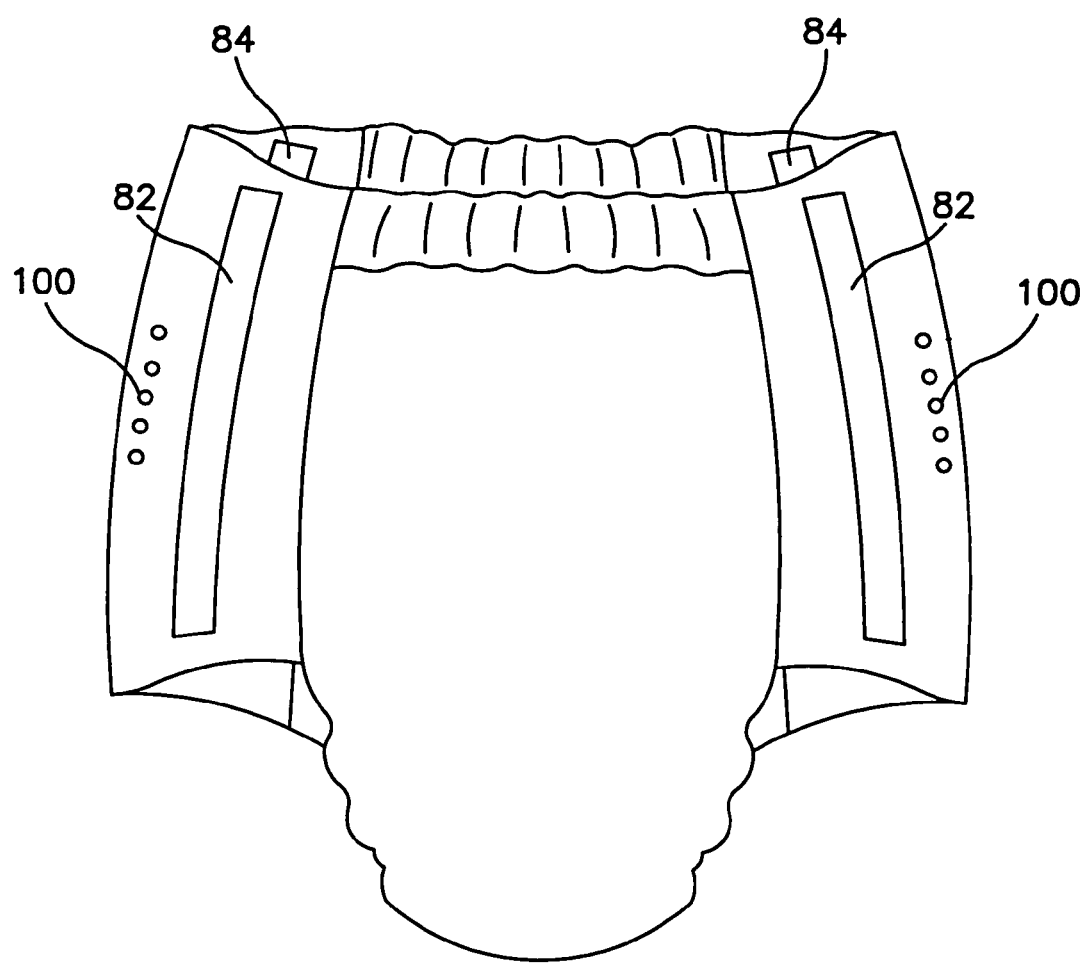
FIG. 7 is a front view of an absorbent garment showing a partial length frangible bond mid-way down the garment connecting the front side panels and the back side panels.

Referring to FIG. 4, each of the frangible bonds 100 can extend substantially from the waist opening 50 to the leg opening 52. Alternatively, each of the frangible bonds 100 can extend a partial distance between the waist opening 50 and the leg opening 52, as shown in FIGS. 6 and 7. The frangible bond 100 can be located anywhere along the length of the front side panels 34 and back side panels 134 between the waist opening 50 and the leg opening 52.

Figure 5A:
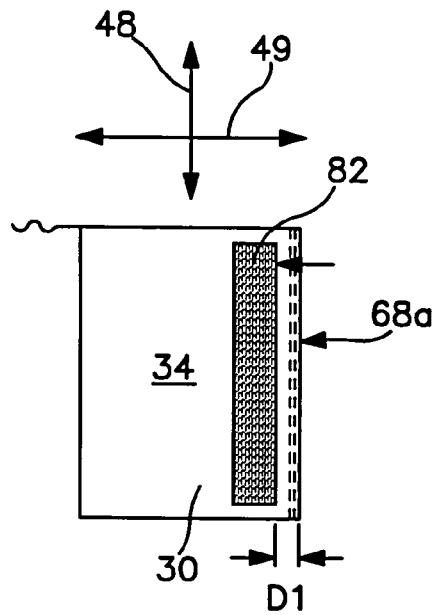
FIG. 5A is a plan view of a front side panel showing the spaced distance between the fastening component and the distal edge of the front side panel.
Figure 5C:
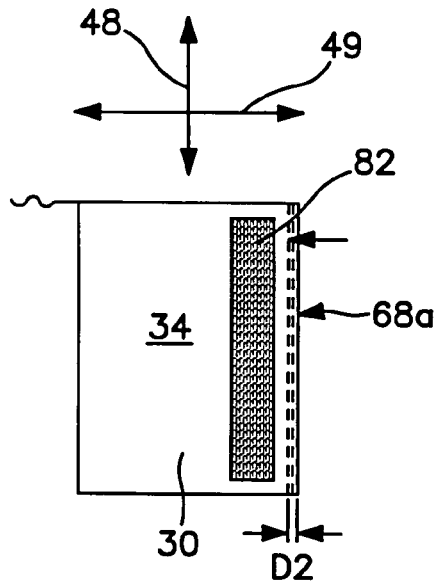
FIG. 5C is a plan view of a front side panel showing the width of the frangible bond.
Figure 5B:
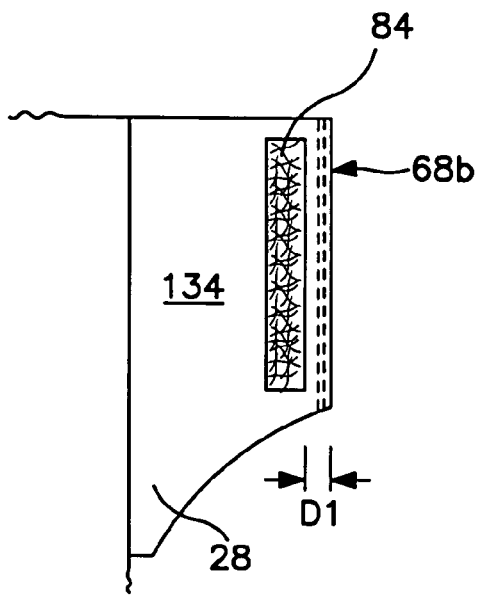
FIG. 5B is a plan view of the back side panel showing the spaced distance between the mating fastening component and the distal edge of the back side panel.

Referring to FIGS. 5A and 5B, each of the fastening components 82 and mating fastening components 84 can be bonded to either the front side panels 34 or back side panels 134 leaving a distance D1 between each fastening component 82 and each distal edge 68a and between each fastening component 84 and each distal edge 68b. The distance D1 provides enough space on each of the front side panels 34 and back side panels 134 for each frangible bond 100. The distance D1 may in particular embodiments be in a range from about 1 mm to about 25 mm, suitably in a range from about 2 mm to about 10 mm, or more particularly in a range from about 3 mm to about 6 mm.

Figure 5D:
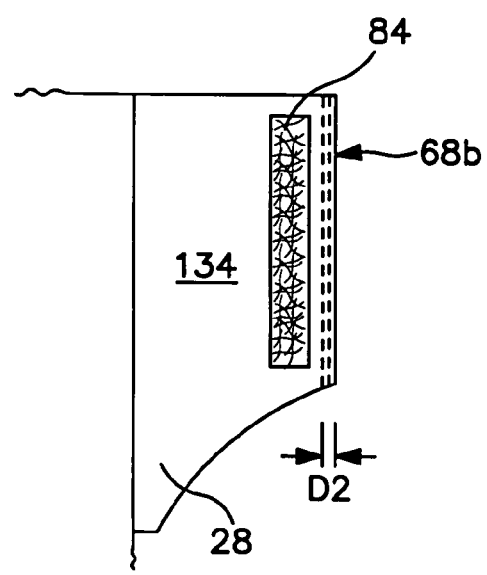
FIG. 5D a plan view of the back side panel showing the width of the frangible bond.

Referring to FIGS. 5C and 5D, each frangible bond 100 has a width D2. Each width D2 may in particular embodiments be in a range from about 1 mm to about 25 mm, suitably in a range from about 2 mm to about 10 mm, or more particularly in a range from about 3 mm to about 6 mm.

As previously mentioned, the frangible bonds 100 are designed to be broken easily by the consumer so that the fastening components 82 and mating fastening components 84 can be fastened to each other, if desired. Alternatively, the consumer can keep the frangible bonds 100 intact and don the product without fastening the fastening components 82 and mating fastening components 84. The frangible bonds 100 may be sufficiently weak that they spontaneously break apart as the product is donned, or alternatively may be strong enough to hold together while the training pant 20 is applied to a wearer. In either case the frangible bonds 100 may be weak enough so that they can be easily broken by the consumer, if desired. According to particular embodiments of the invention, the maximum shear strength of each frangible bond 100 per 76 mm of side panel material in the machine direction (parallel to the transverse axis 49) may be about 3000 grams or less, particularly about 2500 grams or less, particularly about 2000 grams or less, particularly about 1500 grams or less, and more particularly about 1000 grams or less, such as in a range from about 10 grams to about 3000 grams, suitably in a range from about 200 grams to about 2000 grams, or particularly in a range from about 500 grams to about 1000 grams, measured by the Bond Strength Test Procedure.

Figure 8:
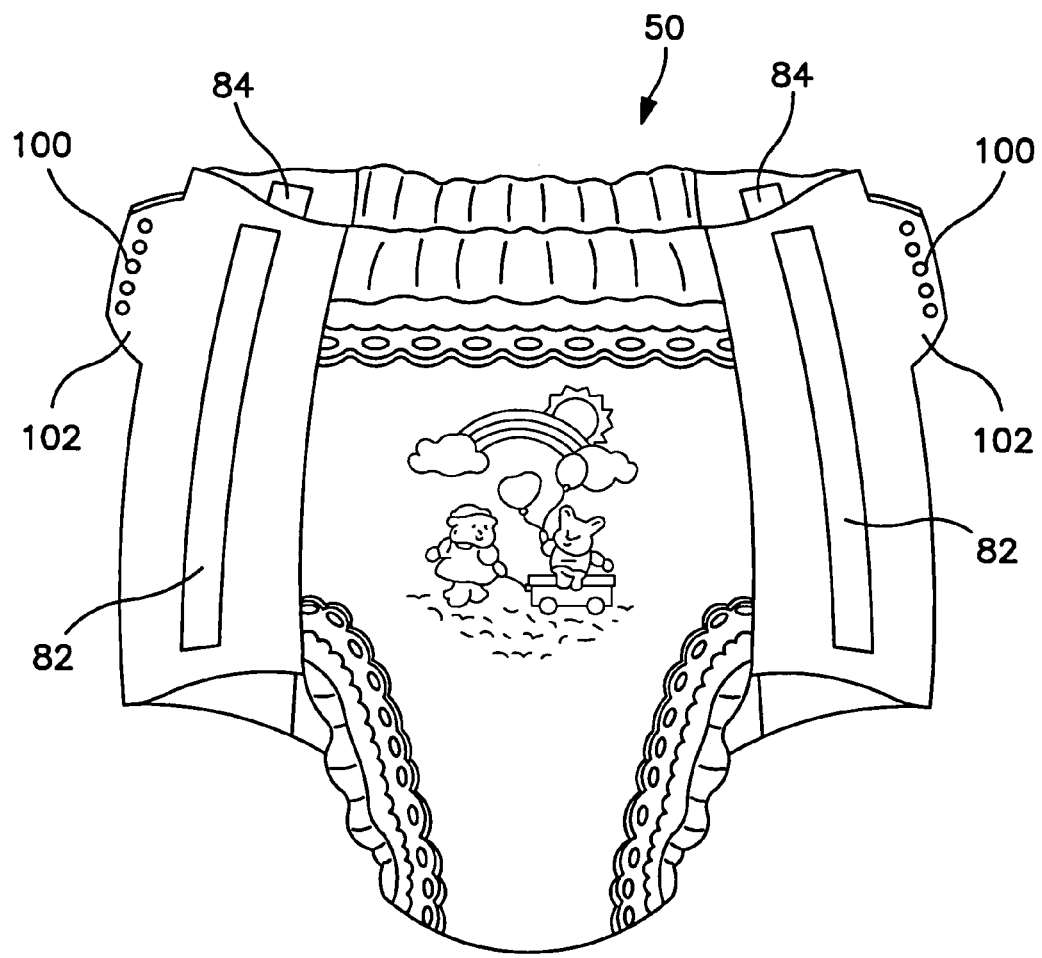
FIG. 8 is a front view of an absorbent garment showing a frangible bond located on a tab adjacent the waist opening.
Figure 9:
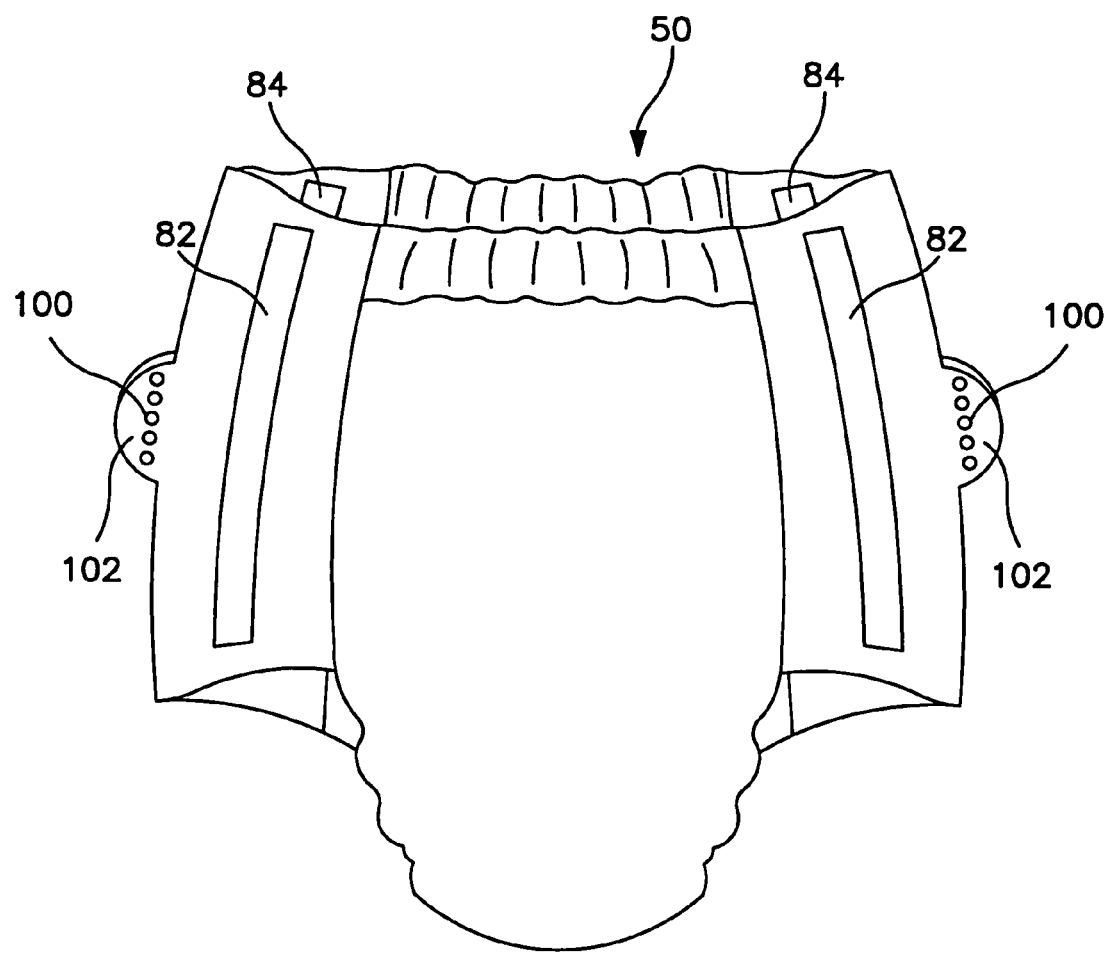
FIG. 9 is front view of an absorbent garment showing a frangible bond located on a tab mid-way down the garment.

Referring to FIGS. 8 and 9, in another embodiment of the invention, the frangible bonds 100 can be located on tabs 102 which extend from the distal edges 68a, 68b of the front side panels and back side panels, 34 and 134. Each front side panel 34 and back side panel can have one or more tabs 102. The frangible bond 100 can be located anywhere along the length of the tabs 102.

Figure 10:
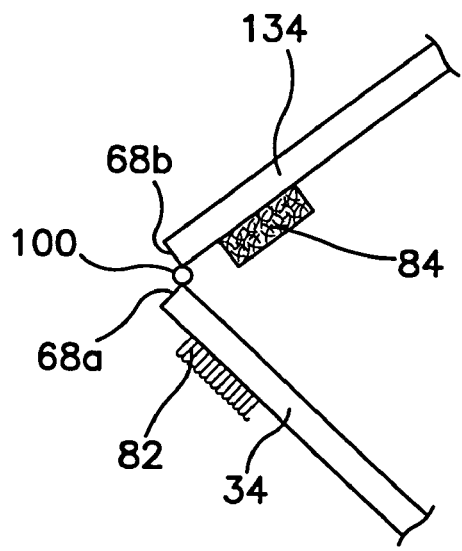
FIG. 10 is an end view of a front side panel and a back side panel showing a frangible bond located between the fastening component and the distal edge of the front side panel and between the mating fastening component and the distal edge of the back side panel.
Figure 11:
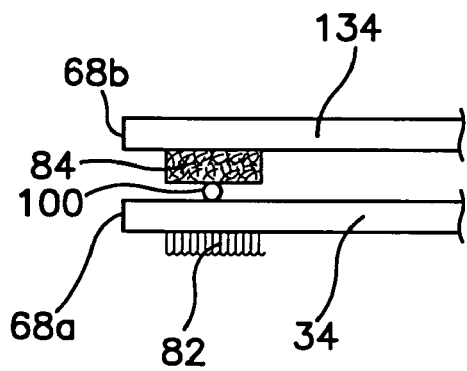
FIG. 11 is an end view of a front side panel and a back side panel showing the frangible bond located through the fastening component and the mating fastening component.
Figure 12:
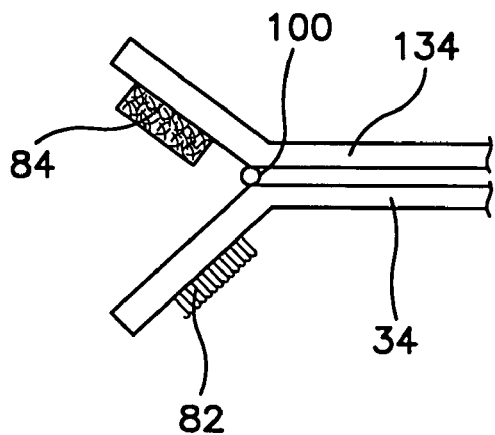
FIG. 12 is an end view of the front side panel and the back side panel showing the frangible bond inward of the fastening component and the mating fastening component.

Referring to FIGS. 10–12, in alternative embodiments of the invention, the location of the frangible bond 100 can vary. For example, in one embodiment, as shown in FIG. 10, the frangible bond 100 can be located between the fastening component 82 and the distal edge 68a of the front side panel 34 and between the mating fastening component 84 and the distal edge 68b of the back side panel 134. In another embodiment, as shown in FIG. 11, the frangible bond 100 can be aligned with the fastening component 82 and the mating fastening component 84. In another embodiment, as shown in FIG. 12, the frangible bond 100 can be located inward of the fastening component 82 and inward of the mating fastening component 84.

Referring to FIGS. 13A–13C and 14A–14C, in alternative embodiments of the invention, either the front side panel 34 or back side panel 134, or both, can include an attachment surface 110 on either the inner surface or the outer surface, or both, or on any other portion of the chassis 32. In these embodiments the fastening system 80 can be modified to include the attachment surfaces 110 which are adapted to refastenably connect either to the fastening components 82 or to the mating fastening components 84, which are bonded to one of the front side panels 34 or the back side panels 134. As previously mentioned with respect to the fastening components 82 and mating fastening components 84, one surface of each of the fastening components 82 and mating fastening components 84 can include a plurality of engaging elements that project from that surface. The engaging elements of the fastening components 82 and the mating fastening components 84 can be adapted to repeatedly engage and disengage the attachment surfaces 110.

Figure 13A:
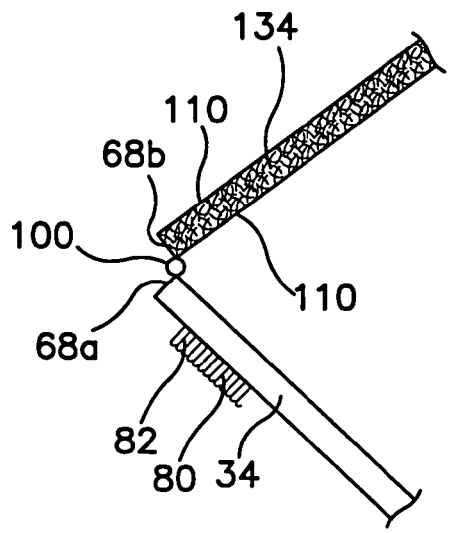
FIG. 13A is an end view of the front side panel including the fastening component on the outer surface and the back side panel including an attachment surface, with the frangible bond located between the fastening component and the distal edge of the front side panel.
Figure 13B:
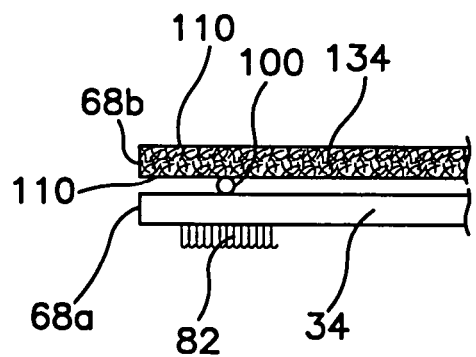
FIG. 13B is an end view of the front side panel including the fastening component on the outer surface and the back side panel including an attachment surface, with the frangible bond located through the fastening component.
Figure 13C:
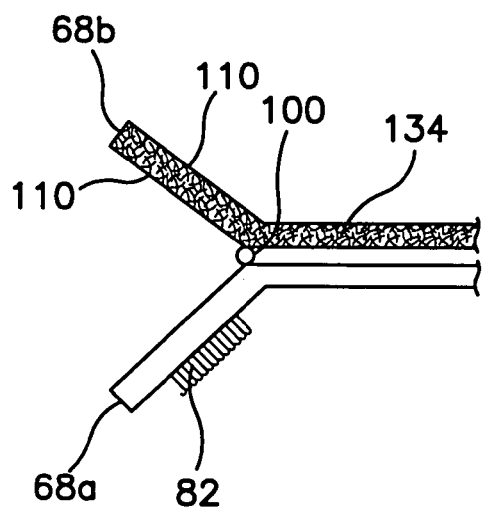
FIG. 13C is an end view of the front side panel including the fastening component on the outer surface and the back side panel including an attachment surface, with the frangible bond located inward of the fastening component.
Figure 14A:
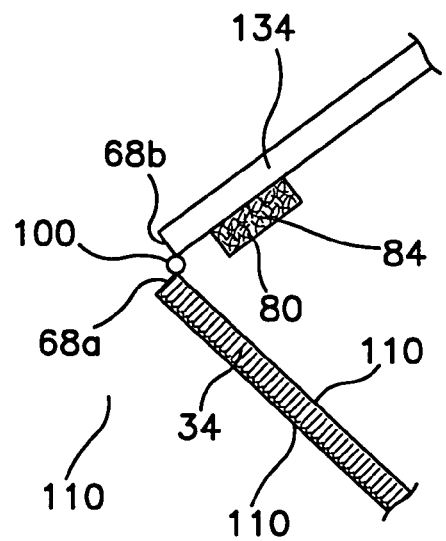
FIG. 14A is an end view of the back side panel including the mating fastening component on the inner surface and the front side panel including an attachment surface, with the frangible bond located between the fastening component and the distal edge of the back side panel.
Figure 14B:
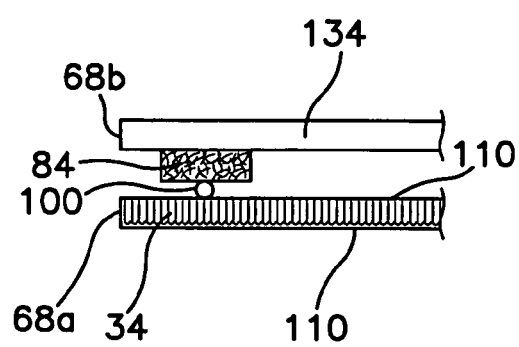
FIG. 14B is an end view of the back side panel including the mating fastening component on the inner surface and the front side panel including an attachment surface, with the frangible bond located through the fastening component.
Figure 14C:
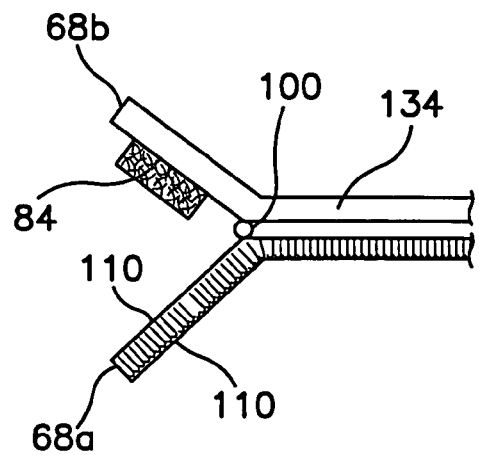
FIG. 14C is an end view of the back side panel including the mating fastening component on the inner surface and the front side panel including an attachment surface, with the frangible bond located inward of the fastening component.
Figure 15A:
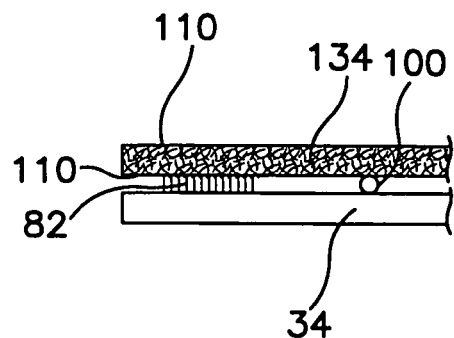
FIG. 15A is an end view of the front side panel including the fastening component on the inner surface and the back side panel including an attachment surface, with the frangible bond located inward of the fastening component.
Figure 15B:
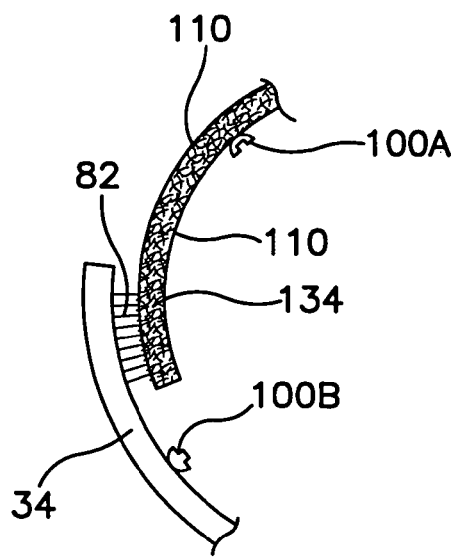
FIG. 15B is an end view showing the frangible bond from FIG. 15A after it has been broken, and the fastening component having been engaged with the attachment surface of the back side panel.
Figure 15C:
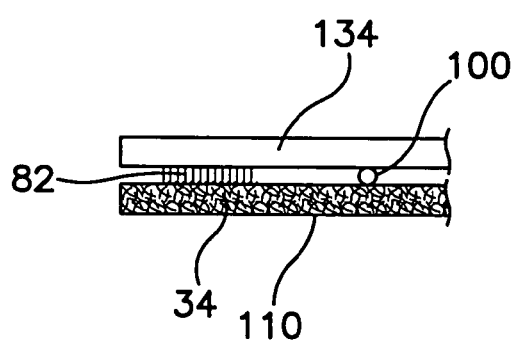
FIG. 15C is an end view of the back side panel including the fastening component on the inner surface and the front side panel including an attachment surface, with the frangible bond located inward of the fastening component.
Figure 15D:
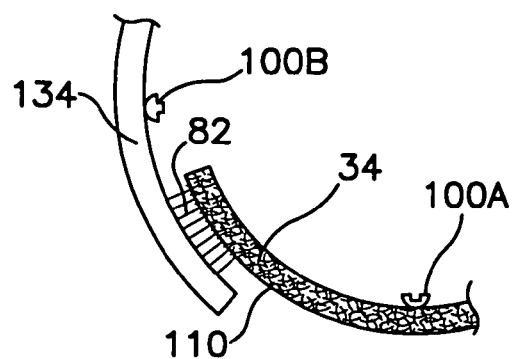
FIG. 15D is an end view showing the frangible bond from FIG. 15C after the bond has been broken and the fastening component having been engaged with the attachment surface of the front side panel.

In one embodiment of the invention, as shown in FIGS. 13A–13C, the fastening components 82 can include hook type fasteners and can be attached to the outer surface of the front side panel 34, and the back side panel 134 can include an attachment surface 110 such as a lofty nonwoven material that is releasably engageable with the hook type fasteners and functions as complementary loop type fasteners. In another embodiment of the invention, as shown in FIGS. 14A–14C, the fastening components 84 can include loop type fasteners and can be attached to the inner surface of the back side panel 134, and the front side panel 34 can include an attachment surface 110 which includes a nonwoven material that is releasably engageably with the loop type fasteners and functions as complementary hook type fasteners.

In this embodiment of the invention, the attachment surfaces 110 can include a variety of woven and nonwoven materials having threads, fibers or protrusions of suitable size and spacing so that the attachment surfaces 110 engage and/or entangle the engaging elements of the fastening components 82 or the mating fastening components 84. In this embodiment of the invention, the front side panels 34 and the back side panels 134 can be constructed of materials that are relatively soft against the wearer's skin and somewhat durable to provide more than one refastenable connection with the fastening components 82 or the mating fastening components 84. The attachment surfaces 110 can include, for example, a spunbond material, a knit fabric, a thermal bonded carded web, a hydroentangled web, or the like that provides several engagements with the fastening components 82 or the mating fastening components 84 prior to significant destruction of the side panel material.

In certain aspects, the modified fastening system 80 of the present embodiment differs from conventional fastening systems and from the fastening system described above for the previous embodiments in that the attachment surfaces 110 do not include separate patches, strips or tabs or fastening component, or mating fastening component material that engage the fastening components 82 or the mating fastening components 84. For example, many conventional fastening systems employ complementary patches, strips or tabs of fastening material, such as hook and loop materials, to form a refastenable connection between the front and back regions 22 and 24.

In contrast, the modified fastening system 80 of the present embodiment, utilizes the attachment surfaces 110 of side panels 34 or 134 to refastenably connect to the fastening components 82 or the mating fastening components 84. This allows the product to have fewer components, which makes the product more underwear-like and provides manufacturing efficiencies. Accordingly, the front side panels 34 and/or the back side panels 134 can consist of, or can consist essentially of, an elastomeric nonwoven material, rather than incorporating separate patches, strips or tabs of fastening component material to engage the fastening components 82 or the mating fastening components 84. The sole means for refastenably connecting the front and back regions 22 and 24 in a pant configuration can consist of the mechanical fastening elements, fastening components 82 or mating fastening components 84, on either the front side panels or back side panels 34, 134, and the attachment surfaces 110 on the other of the front side panels or back side panels 34, 134.

The embodiments of the training pant 20 depicted in FIGS. 13A–13C and 14A–14C can further include a frangible bond 100 connecting each front side panel 34 and each back side panel 134. Referring to FIGS. 13A–13C and 14A–14C, as in embodiments described in FIGS. 10–12 above, the location of the frangible bond 100 can vary. For example, in one embodiment, as shown in FIGS. 13A and 14A, the frangible bond 100 can be located between the fastening component 82, or the mating fastening component 84, and the distal edge 68a of the front side panel 34 or the distal edge 68b of the back side panel 134. In another embodiment, as shown in FIGS. 13B and 14B, the frangible bond 100 can be located through the fastening component 82 or the mating fastening component 84. In another embodiment, as shown in FIGS. 13C and 14C, the frangible bond 100 can be located inward of the fastening component 82 or the mating fastening component 84.

As shown in FIGS. 15A–15D, the frangible bond 100 connecting the front side panel 34 and the back side panel 134 can be broken and the fastening component 82 located on either the front side panel 34 or the back side panel 134 can be refastenably engaged to the attachment surface 110 on the other of the front side panel 34 or the back side panel 134. Broken bond pieces 100A and 100B are shown to illustrate the location of the previously intact frangible bond 100 connecting the front and back side panels, 34 and 134.

Figure 16A:
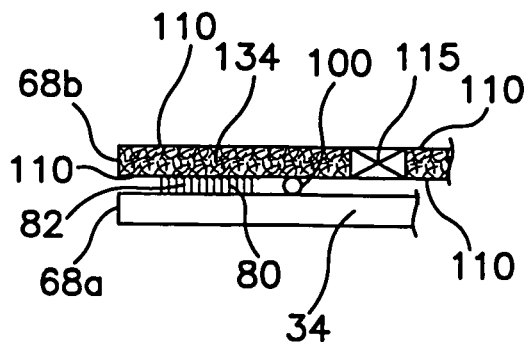
FIG. 16A is an end view of the front side panel including the fastening component on the inner surface and the back side panel including an attachment surface and a perforation located inward of the frangible bond.
Figure 16B:
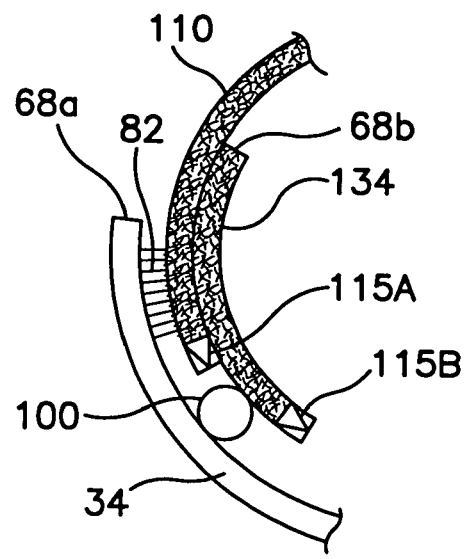
FIG. 16B is an end view showing the perforation from FIG. 16A after the perforation has been broken, with the frangible bond still intact, and a broken edge of the perforation having been inserted between the distal edge of the front side panel and the distal edge of the back side panel.
Figure 16C:
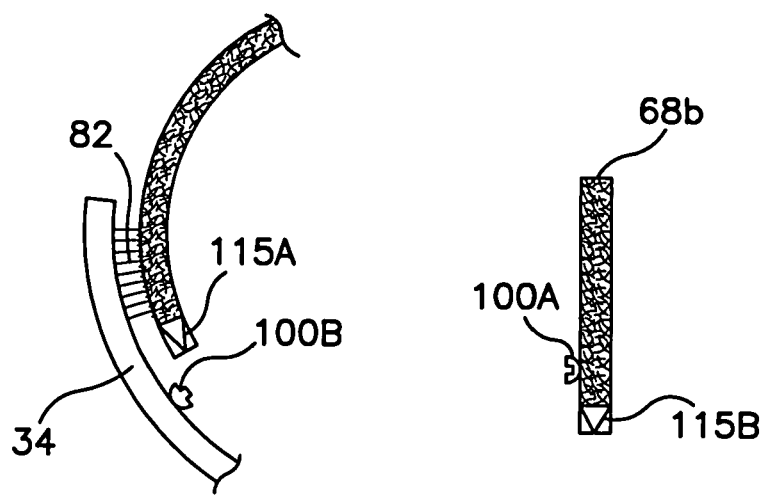
FIG. 16C is an end view showing the frangible bond from FIG. 16B after the bond has been broken and the free piece of the back side panel that results.
Figure 17A:
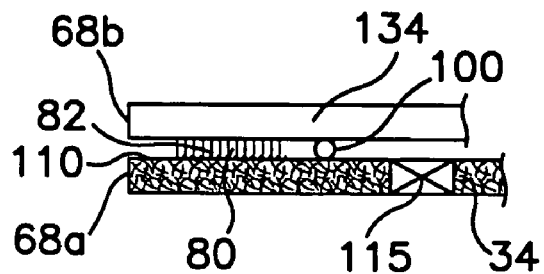
FIG. 17A is an end view of the back side panel including the fastening component on the inner surface and the front side panel including an attachment surface and a perforation located inward of the frangible bond.
Figure 17B:
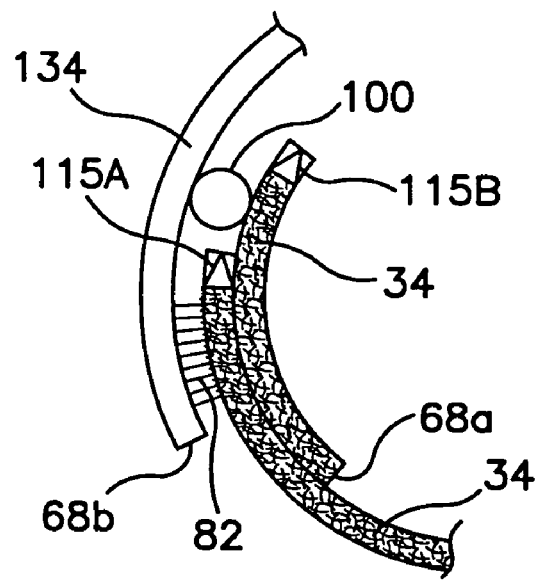
FIG. 17B is an end view showing the perforation from FIG. 17A after the perforation has been broken, with the frangible bond still intact, and the broken edge of the perforation having been inserted between the distal edge of the front side panel and the distal edge of the back side panel.
Figure 17C:
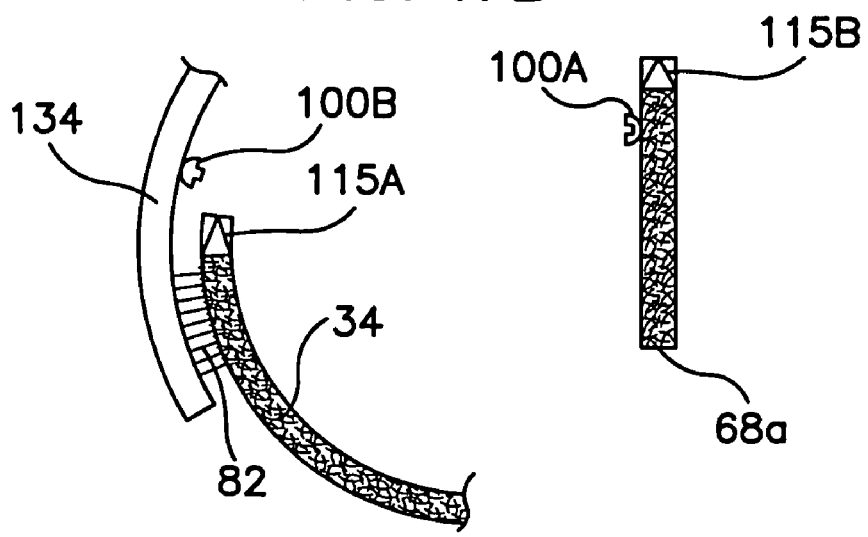
FIG. 17C is an end view showing the frangible bond from FIG. 17B after the bond has been broken and the free piece of the back side panel that results.
Figure 18A:
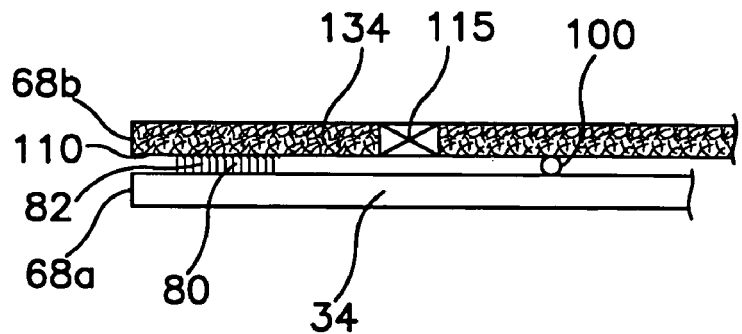
FIG. 18A is an end view of the front side panel including the fastening component on the inner surface and the back side panel including an attachment surface and a perforation located outward of the frangible bond.
Figure 18B:
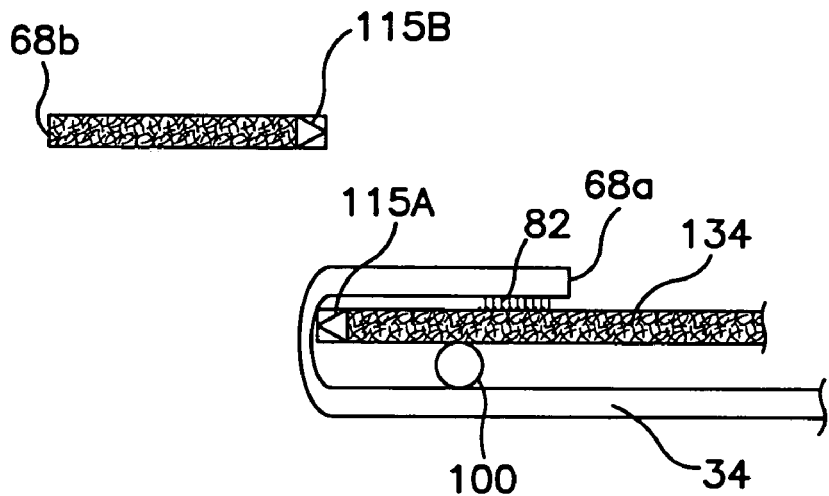
FIG. 18B is an end view showing the perforation from FIG. 18A after the perforation has been broken, with the frangible bond still intact, and the free piece of material that results from the breaking of the perforation.
Figure 18C:
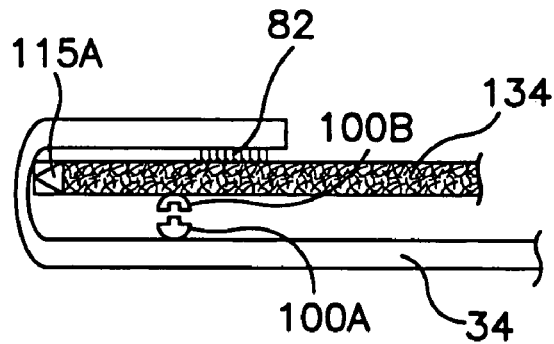
FIG. 18C is an end view showing the frangible bond from FIG. 18B after the bond has been broken.
Figure 19A:
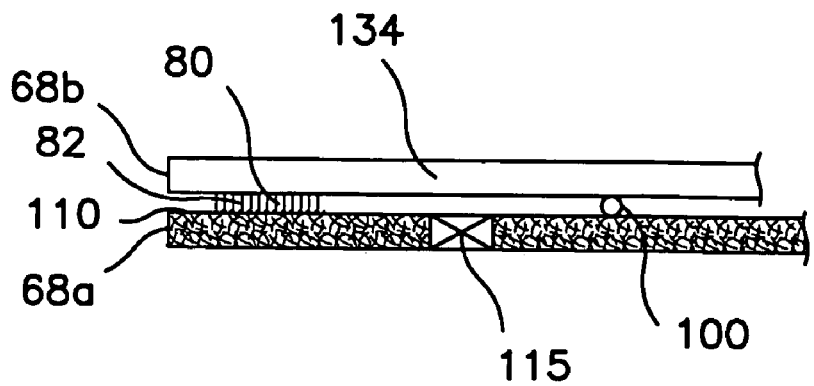
FIG. 19A is an end view of the back side panel including the fastening component on the inner surface and the front side panel including an attachment surface and a perforation located outward of the frangible bond.

Referring to FIGS. 16A–16C, 17A–17C, 18A–18C, and 19A–19C, in still further embodiments of the invention, the front side panels 34 or the back side panels 134 can optionally include a perforation 115. As shown in FIGS. 16A and 17A, the perforation 115 can be located inward of the frangible bond 100. Alternatively, as shown in FIGS. 18A and 19A, the perforation 115 can be located outward of the frangible bond 100.

Referring again to FIGS. 16A–16C, as in the embodiments discussed above, the consumer has the option of donning the product with the frangible bond 100 intact. In the embodiments that include the perforation 115, the consumer has the further option of donning the product with the perforation 115 intact. In the alternative, the consumer has the option of breaking the perforation 115 and employing the fastening system 80.

As shown in FIGS. 16A–16B and 17A–17C, when the perforation 115 is located inward of the frangible bond 100, the consumer can break the perforation 115. Broken perforation ends 115A and 115B are shown to illustrate the location of the previously intact perforation 115. The consumer can then pull broken perforation end 115A around and insert it between the distal edges 68a and 68b so that the attachment surface 110 releasably connects to the fastening component 82, while leaving the frangible bond 100 intact. The stretch of back side panel 134 between the distal edge 68b and the broken perforation end 115B remains attached because the frangible bond 100 is still intact. As shown in FIGS. 16C and 17C, if the frangible bond 100 is broken, the stretch of back side panel 134 between the distal edge 68b and the broken perforation end 115B becomes detached and free from the training pant 20. Broken bond pieces 100A and 100B are shown to illustrate the location of the previously intact frangible bond 100 connecting the front and back side panels 34 and 134. The free piece of back side panel 134 can optionally be discarded by the consumer.

Figure 19B:
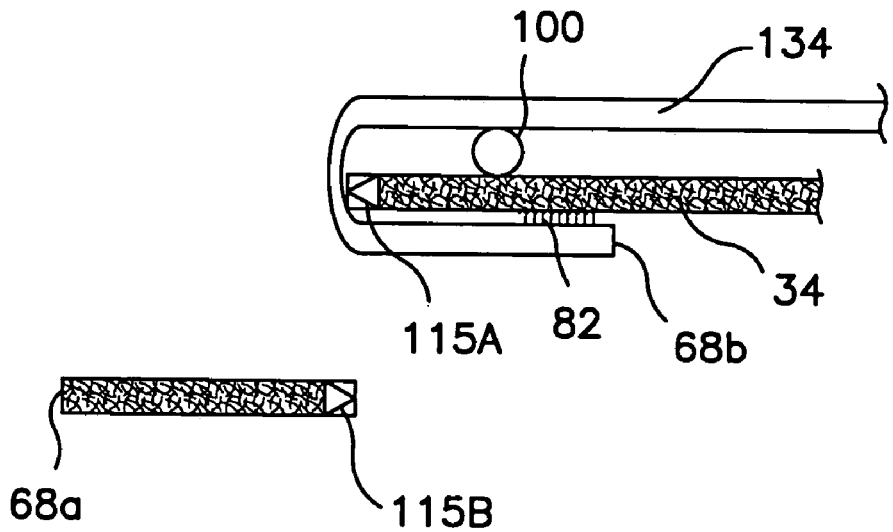
FIG. 19B is an end view showing the perforation from FIG. 19A after the perforation has been broken, with the frangible bond still intact, and the free piece of material that results from the breaking of the perforation.
Figure 19C:
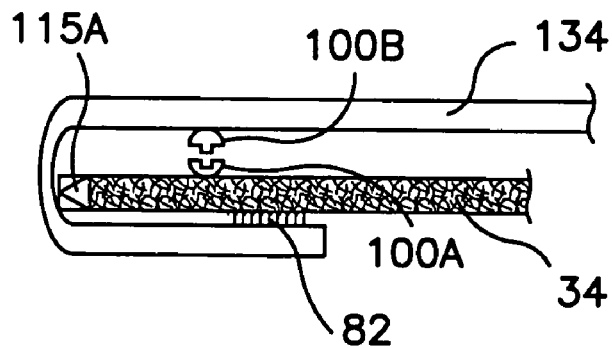
FIG. 19C is an end view showing the frangible bond from FIG. 19B after the has been broken.

As shown in FIGS. 18A–18C and 19A–19C, when the perforation 115 is located outward of the frangible bond 100, the consumer can also break the perforation 115. Broken perforation ends 115A and 115B are shown to illustrate the location of the previously intact perforation 115. The consumer can then remove the stretch of back side panel 134 between the distal edge 68b and the broken perforation end 115B and releasably connect the fastening component 82 to the attachment surface 110, while leaving the frangible bond 100 intact. However, the stretch of back side panel 134 between the distal edge 68b and the broken perforation end 115B becomes detached and free from the training pant even with the frangible bond 100 still intact, as shown in FIGS. 18B and 19B, because of the location of the perforation 115 outward of the frangible bond 100. As shown in FIGS. 18C and 19C, the frangible bond 100 can also be broken. Broken bond pieces 100A and 100B are shown to illustrate the location of the previously intact frangible bond 100 connecting the front and back side panels 34 and 134. The free piece of back side panel 134 can optionally be discarded by the consumer.

As previously mentioned, the frangible bonds 100 must be strong enough to hold together while the training pant 20 is applied to a wearer, but weak enough so that they can be easily broken by the consumer, if desired. According to particular embodiments of the invention, the maximum shear strength of each frangible bond 100 per 76 mm of side panel material in the machine direction (parallel to the transverse axis 49) may be about 3000 grams or less, particularly about 2500 grams or less, particularly about 2000 grams or less, particularly about 1500 grams or less, and more particularly about 1000 grams or less, such as in a range from about 10 grams to about 3000 grams, suitably in a range from about 200 grams to about 2000 grams, or alternatively in a range from about 500 grams to about 1000 grams, measured by the Bond Strength Test Procedure.

Figure 20A:
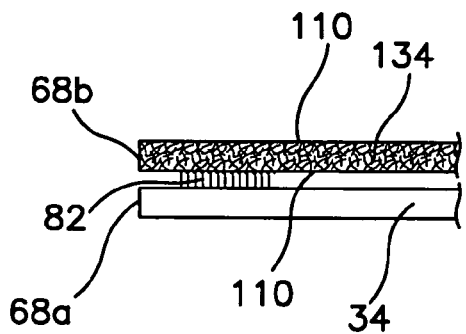
FIG. 20A is an end view of another embodiment of the invention showing the front side panel including the fastening component on the inner surface and the back side panel including an attachment surface.
Figure 20B:
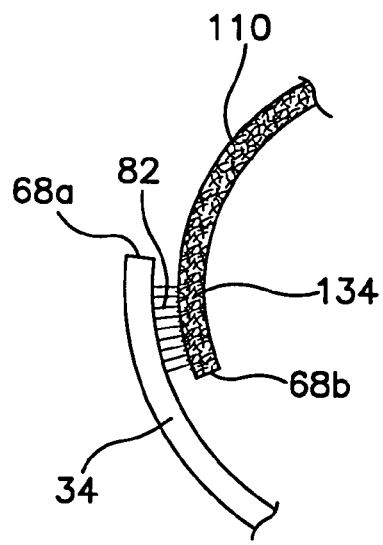
FIG. 20B is an end view showing the embodiment of FIG. 20A with the fastening component refastenably engaged to the attachment surface of the back side panel.
Figure 20C:
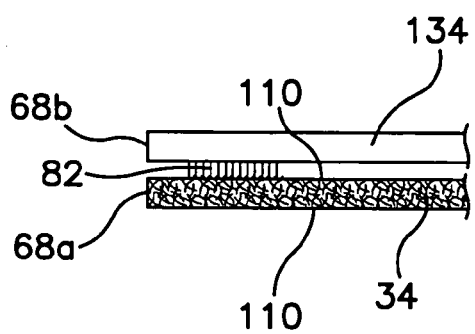
FIG. 20C is an end view showing the back side panel including the fastening component on the inner surface and the front side panel including an attachment surface.
Figure 20D:
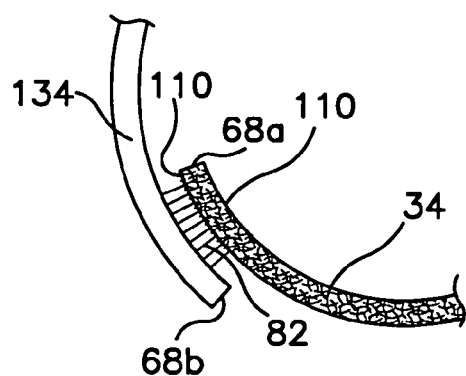
FIG. 20D is an end view showing the embodiment of FIG. 20C with the fastening component refastenably engaged to the attachment surface of the front side panel.

Referring to FIGS. 20A–20D, in a still further embodiment of the invention, the front side panels 34 or the back side panels 134 can include attachment surfaces 110 and the other of the front side panels 34 or the back side panels 134 can include either a fastening component 82 or mating fastening component 134. Both the inner and the outer surfaces of the front side panels 34 or the back side panels 134 without the fastening component 82 or mating fastening component 84 defines an attachment surface 110 adapted to refastenably engage the fastening component 82 or mating fastening component 84. In this embodiment, no frangible bond connects the front and back side panels 34 and 134 and neither the front side panels 34 nor the back side panels 134 have a perforation. In this embodiment, the fastening component 82 or the mating fastening component 84 is located on the inner surface of the front side panel 34 or the inner surface of the back side panel 134. Without the presence of the frangible bond connecting the front and back side panels 34 and 134, the product will be less easy to don in a pant-like configuration without engaging the fastening component 82 and the attachment surface 110 as shown in FIGS. 20B and 20D. However, as shown in FIGS. 20A and 20C the inner surfaces of each front side panel 34 and corresponding back side panel 134 face, and lie flat upon each other so that the attachment surface 110 of each front side panel 34 or back side panel 134 contacts and engages the fastening component 82 on the inside surface of the other of the front side panel 34 or the back side panel 134. The front and back side panels 34 and 134, therefore, do not need to be folded or manipulated in any way in order to engage the fastening components in the manufacturing process.

As described herein, the various components of the absorbent garment 20 can be integrally assembled together employing various types of suitable attachment means, such as adhesive, sonic and thermal bonds or combinations thereof. The resulting product is an absorbent garment having refastenable side seams that can be opened for donning or removal at either side of the garment.

TEST METHOD: BOND STRENGTH

This procedure is a bench test to determine the breaking strength of the seam on a garment when the garment is elongated at a constant rate in a direction perpendicular to the direction of the seam. The method is designed to test for peak load at the breaking point of the bond.

1. Overview

A material sample is placed between clamps on a tensile tester; the width of the material to be tested is 3 inches (76 mm). The gage length is 2 inches (51 mm) between the ends of the clamp faces. The term "load" refers to the force value measured by the load cells in the tensile tester.

NOTE: When the material is less than 3 inches (76 mm) wide, cut the sample from the side of the product so that the bond is fully within the sample.

The material to be tested is cut to provide a uniform 3 inch (76 mm) sample width, parallel to the direction of the seam bond(s) on the material. Samples should be at least 4 inches (102 mm) in length (perpendicular to the seam), with the seam centered in this distance.

The jaws are separated until the seam is torn apart. The load values generated on the material throughout this process are recorded. If slippage of specimens between the jaws occurs during testing, the grip faces of the jaws can be adapted to increase friction with specimens.

2. Apparatus and Materials 2.1 Constant Rate of Extension (CRE) tensile tester: MTS tensile tester model Synergie 200 Test Bed; available from MTS® Systems Corporation, Research Triangle Park, N.C. USA.

2.2 Load cells: A suitable cell selected so the majority of the peak load values fall between the manufacturer's recommended ranges of load cell's full scale value such as a 100N load cell available from MTS® Systems Corporation, Research Triangle Park, N.C. USA.

2.3 Operating software and data acquisition system: MTS TestWorks® for Windows software version 4; available from MTS® Systems Corporation, Research Triangle Park, N.C. USA.

2.4 Grips: pneumatic-action grips, top and bottom, identified as part number 2712-003 available from Instron Corporation, Canton, Mass. USA.

2.5 Grip faces: flat faces, 25 by 75-mm (1 by 3-inch).

3. Conditioning

Conduct test in standard ASTM laboratory conditions: atmosphere of 23±2° C. (73.4±3.6° F.) and 50±5% relative humidity. The products should be measured after they equilibrate to laboratory conditions.

4. Test Specimen

A material specimen that is at least 4 inches (102 mm) in length (the direction of tensile testing) and is 3 inches (76 mm) in width (perpendicular to testing) should be used.

At least ten specimens of each sample should be tested, and the results averaged.

5. Procedure

| Tensile Tester test conditions: | |
|---|---|
| Break sensitivity | 90% drop from peak load |
| Break threshold | 227 g of force |
| Data acquisition rate | 100 Hz |
| Extension endpoint | 25 mm |
| Gage adjustment pre-load | 0.100 lbs of force |
| Gage adjustment speed | 2.5 mm/min |
| Test speed | 500 mm/min |
| Load endpoint | 2000 g |
| Gage length: | 2 inches (51 mm) |

A. Calibrate the load cell using the Testworks software, at the beginning of each work session.

B. Using the tensile frame pushbutton controls for crosshead position, move grips to provide a gage length of 2 inches (51 mm). Calibrate the software to this initial gage length.

C. Zero the load cell before each sample, or whenever the load cell appears to be drifting; no specimens should be in the cell when it is zeroed.

D. Place a material specimen so that it is centered between the grips, held in a centered position within each grip, and oriented correctly (3 inch/76 mm dimension running the width direction on the grips, approximately 1 inch of material held in each grip, and the seam centered between the grip faces). The specimen's seam should be parallel to the grip faces, and the vertical edges should be perpendicular to the grip faces.

E. Close the grips on the specimen, holding the specimen in such a way as to minimize slack in the specimen, but do not place the specimen under tension. Ensure that the load at this point is less than five grams. If the load is greater than five grams, release the lower grip. Reclose the lower grip, again ensuring that the specimen is neither under tension nor buckled with excessive slack. Continue checking the starting load and following the above procedure until the starting load is under five grams. If the load cell is not below five grams when the sample is suspended from only the top grip, return to step C and zero the load cell.

F. Run the single cycle test using the above parameters by clicking on the RUN button.

G. When the test is complete, save the data to a sample file.

H. Remove the specimen from the grips.

I. Run additional specimens of a given sample using steps D–F and H; the data for all specimens should be saved to a single file.

J. Continue testing all samples in this manner.

K. Report the average peak load for each sample.

| | | | | Side Panel Bond Strengths | | | | |
|---|---|---|---|---|---|---|---|---|
| Manufacturer | Brand | Gender | Size | Side | Test Date | Avg., g. | Std. Dev.., g. | Replicates |
| Drypers | Next Step | Unisex | 32–40 lbs. | Left | 4 Q 2000 | 3500 | 700 | 10 |
| Drypers | Next Step | Unisex | 32–40 lbs. | Right | 4 Q 2000 | 3900 | 600 | 10 |
| Paragon | White Cloud | Girl | 32–40 lbs. | Left | 4 Q 2000 | 3700 | 400 | 10 |
| Paragon | White Cloud | Girl | 32–40 lbs. | Right | 4 Q 2000 | 3400 | 500 | 10 |
| Paragon | White Cloud | Boy | 32–40 lbs. | Left | 4 Q 2000 | 3600 | 700 | 10 |
| Paragon | White Cloud | Boy | 32–40 lbs. | Right | 4 Q 2000 | 3500 | 390 | 10 |
| Procter & Gamble | Sukusuku | Unisex | 12 + kg | Left | 4 Q 2000 | 4900 | 400 | 10 |
| Procter & | Sukusuku | Unisex | 12 + kg | Right | 4 Q 2000 | 4700 | 200 | 10 |

-continued

Side Panel Bond Strengths

| Manufacturer | Brand | Gender | Size | Side | Test Date | Avg., g. | Std. Dev.., g. | Replicates |
|---|---|---|---|---|---|---|---|---|
| Procter & Gamble | First Steps | Unisex | 12 + kg | Left | 1 Q 2001 | 3900 | 300 | 10 |
| Procter & Gamble | First Steps | Unisex | 12 + kg | Right | 1 Q 2001 | 4000 | 300 | 10 |
| Procter & Gamble | First Steps | Unisex | 12 + kg | Left | 1 Q 2001 | 4600 | 400 | 20 |
| Procter & Gamble | First Steps | Unisex | 12 + kg | Right | 1 Q 2001 | 4500 | 500 | 20 |
| Kimberly-Clark | Pull-Ups ® (Note 1) | Girl | 32–40 lbs. | Left | 1 Q 2001 | 4500 | 500 | 20 |
| Kimberly-Clark | Pull-Ups ® (Note 1) | Girl | 32–40 lbs. | Right | 1 Q 2001 | 4800 | 200 | 20 |
| Kimberly-Clark | Pull-Ups ® (Note 1) | Boy | 32–40 lbs. | Left | 1 Q 2001 | 4300 | 300 | 20 |
| Kimberly-Clark | Pull-Ups ® (Note 1) | Boy | 32–40 lbs. | Right | 1 Q 2001 | 4800 | 300 | 20 |
| Kimberly-Clark | Pull-Ups ® (Note 2) | Girl | 32–40 lbs. | Left | 1 Q 2001 | 4300 | 300 | 20 |
| Kimberly-Clark | Pull-Ups ® (Note 2) | Girl | 32–40 lbs. | Right | 1 Q 2001 | 4700 | 300 | 20 |
| Kimberly-Clark | Pull-Ups ® (Note 2) | Boy | 32–40 lbs. | Left | 1 Q 2001 | 4300 | 300 | 20 |
| Kimberly-Clark | Pull-Ups ® (Note 2) | Boy | 32–40 lbs. | Right | 1 Q 2001 | 4900 | 300 | 20 |

Note 1:
PULL-UPS ® training pants new product design commercialized in 1 Q 2001
Note 2:
PULL-UPS ® training pants product design prior to 1 Q 2001
Note 3:
Results rounded to nearest 100 grams It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A disposable garment comprising:
    at least one front side panel comprising a fastening component, the front side panel defining a distal edge;
    at least one back side panel comprising a mating fastening component, the back side panel defining a distal edge;
    at least one frangible bond connecting the front side panel and the back side panel, the fastening component and the mating fastening component being in the unfastened condition;
    wherein the at least one frangible bond is located between the fastening component and the distal edge of the front side panel and between the mating fastening component and the distal edge of the back side panel.

2. The disposable garment of claim 1, further comprising at least one first opening and at least one second opening.

3. The disposable garment of claim 2 wherein the frangible bond extends substantially from the first opening to the second opening.

4. The disposable garment of claim 2 wherein the frangible bond extends a partial distance from the first opening to the second opening.

5. The disposable garment of claim 1 wherein the frangible bond has a width in a range from about 1 mm to about 25 mm.

6. The disposable garment of claim 1 wherein the frangible bond has a width in a range from about 2 mm to about 10 mm.

7. The disposable garment of claim 1 wherein the frangible bond has a width in a range from about 3 mm to about 6 mm.

8. The disposable garment of claim 1 wherein a strength of the frangible bond is in a range from about 10 grams to about 2700 grams.

9. The disposable garment of claim 1 wherein a strength of the frangible bond is less than about 2700 g.

10. The disposable garment of claim 1 wherein a strength of the frangible bond is in a range from about 200 grams to about 2000 grams.

11. The disposable garment of claim 1 wherein a strength of the frangible bond is less than about 2000 g.

12. The disposable garment of claim 1 wherein a strength of the frangible bond is in a range from about 500 grams to about 1000 grams.

13. The disposable garment of claim 1 wherein a strength of the frangible bond is less than about 1000 g.

14. An absorbent garment, comprising:
- a chassis including a first front side panel and a second front side panel, a first back side panel and a second back side panel, and defining a waist opening and first and second leg openings;
- each front side panel having an inner surface and an outer surface and defining a distal edge;
- each back side panel having an inner surface and an outer surface and defining a distal edge;
- a first frangible bond connecting the first front side panel and the first back side panel;
- a second frangible bond connecting the second front side panel and the second back side panel;
- wherein each of the front side panels comprises a fastening component bonded to one of the inner and the outer surfaces adjacent the distal edge of the front side panel, and each of the back side panels comprises a mating fastening component bonded to one of the inner and the outer surfaces adjacent the distal edge of the back side panel, the fastening component and the mating fastening component being in the unfastened condition;
- wherein each of the front side panels defines a distance between the fastening component and the distal edge, and each of the back side panels defines a distance between the mating fastening component and the distal edge; and
- wherein the first frangible bond is located between the fastening component and the distal edge of the first front side panel and between the mating fastening component and the distal edge of the first back side panel; and
- wherein the second frangible bond is located between the fastening component and the distal edge of the second front side panel and between the mating fastening component and the distal edge of the second back side panel.

15. The absorbent garment of claim 14 wherein the first frangible bond extends substantially from the waist opening to the first leg opening, and the second frangible bond extends substantially from the waist opening to the second leg opening.

16. The absorbent garment of claim 14 wherein the first frangible bond extends a partial distance from the waist opening to the first leg opening, and the second frangible bond extends a partial distance from the waist opening to the second leg opening.

17. The absorbent garment of claim 14 wherein the distance between each of the fastening components and the distal edge of one of the front side panels is in a range from about 1 mm to about 25 mm.

18. The absorbent garment of claim 14 wherein the distance between each of the mating fastening components and the distal edge of one of the back side panels is in a range from about 1 mm to about 25 mm.

19. The absorbent garment of claim 14 wherein the distance between each of the fastening components and the distal edge of one of the front side panels is in a range from about 2 mm to about 10 mm.

20. The absorbent garment of claim 14 wherein the distance between each of the mating fastening components and the distal edge of one of the back side panels is in a range from about 2 mm to about 10 mm.

21. The absorbent garment of claim 14 wherein the distance between each of the fastening components and the distal edge of one of the front side panels is in a range from about 3 mm to about 6 mm.

22. The absorbent garment of claim 14 wherein the distance between each of the mating fastening components and the distal edge of one of the back side panels is in a range from about 3 mm to about 6 mm.

23. The absorbent garment of claim 14 wherein each of the first and second frangible bonds have a width in a range from about 1 mm to about 25 mm.

24. The absorbent garment of claim 14 wherein a strength of each of the frangible bonds is less than about 2700 grams.

25. The absorbent garment of claim 14 wherein a strength of each of the frangible bonds is less than about 2000 grams.

26. The absorbent garment of claim 14 wherein a strength of each of the frangible bonds is in a range from about 500 grams to about 1000 grams.

27. An absorbent garment, comprising:
- a chassis including a first front side panel and a second front side panel, a first back side panel and a second back side panel, defining a waist opening and first and second leg openings, and each front side panel and each back side panel having an inner surface and an outer surface;
- each front side panel defining a distal edge;
- each back side panel defining a distal edge;
- a first frangible bond connecting the first front side panel and the first back side panel; and
- a second frangible bond connecting the second front side panel and the second back side panel;
- each front side panel and each back side panel having a nonwoven substrate and at least one of the front side panels and the back side panels defining an attachment surface; and
- at least one fastening component bonded to one of the front side panels and the back side panels on one of the inner surface and the outer surface, the at least one fastening component comprising a mechanical fastening element adapted to refastenably engage the attachment surface, the mechanical fastening element and the attachment surface being in the unfastened condition;
- wherein each frangible bond is located between the mechanical fastening element and the distal edge of the side panel comprising the mechanical fastening element.

28. The absorbent garment of claim 27 wherein the at least one fastening component is bonded to the inner surface of the chassis.

29. The absorbent garment of claim 27 wherein the at least one fastening component is bonded to the outer surface of the chassis.

30. The absorbent garment of claim 27 wherein the attachment surface comprises complementary loop fasteners.

31. The absorbent garment of claim 27 wherein the attachment surface comprises complementary hook fasteners.

32. The absorbent garment of claim 27 wherein each of the first and second frangible bonds have a width in a range from about 1 mm to about 25 mm.

33. The absorbent garment of claim 27 wherein each of the first and second frangible bonds have a width in a range from about 2 mm to about 10 mm.

34. The absorbent garment of claim 27 wherein a strength of each of the frangible bonds is less than about 2700 grams.

35. The absorbent garment of claim 27 wherein a strength of each of the frangible bonds is less than about 2000 grams.

36. The absorbent garment of claim 27 wherein a strength of each of the frangible bonds is in a range from about 500 grams to about 1000 grams.

37. An absorbent garment, comprising:
a chassis including a first front side panel and a second front side panel, a first back side panel and a second back side panel, defining a waist opening and first and second leg openings, and each front side panel and each back side panel having an inner surface and an outer surface;
each front side panel defining a distal edge;
each back side panel defining a distal edge;
a first frangible bond connecting the first front side panel and the first back side panel; and
a second frangible bond connecting the second front side panel and the second back side panel;
each front side panel and each back side panel having a nonwoven substrate and at least one of the front side panels and the back side panels defining an attachment surface; and
at least one fastening component bonded to one of the front side panels and the back side panels on one of the inner surface and the outer surface, the at least one fastening component comprising a mechanical fastening element adapted to refastenably engage the attachment surface, the mechanical fastening element and the attachment surface being in the unfastened condition wherein one of each front side panel and each back side panel further comprises a perforation.

38. The absorbent garment of claim 37 wherein each perforation is located inward of each frangible bond.

39. The absorbent garment of claim 37 wherein each perforation is located outward of the each frangible bond.

40. An absorbent garment, comprising:
a chassis including a first front side panel and a second front side panel, a first back side panel and a second back side panel, defining a waist opening and first and second leg openings, and each front side panel and each back side panel having an inner surface and an outer surface;
each front side panel defining a distal edge;
each back side panel defining a distal edge;
a first frangible bond connecting the first front side panel and the first back side panel; and
a second frangible bond connecting the second front side panel and the second back side panel;
a portion of the chassis having a nonwoven substrate defining an attachment surface; and
at least one fastening component bonded to one of the front side panels and the back side panels on one of the inner surface and the outer surface, the at least one fastening component comprising a mechanical fastening element adapted to refastenably engage the attachment surface, the mechanical fastening element and the attachment surface being in the unfastened condition;
wherein each frangible bond is located between the mechanical fastening element and the distal edge of the side panel comprising the mechanical fastening element.

41. The absorbent garment of claim 40 wherein a strength of each of the frangible bonds is less than about 2700 grams.

42. The absorbent garment of claim 40 wherein a strength of each of the frangible bonds is less than about 2000 grams.

43. An absorbent garment, comprising:
a chassis including a first front side panel and a second front side panel, a first back side panel and a second back side panel, and each front side panel and each back side panel having an inner surface and an outer surface;
one of the front side panels and the back side panels comprising a nonwoven substrate and defining an attachment surface; and
at least one fastening component bonded to the inner surface of one of the front side panels and the back side panels, the at least one fastening component comprising a mechanical fastening element adapted to refastenably engage the attachment surface;
wherein the at least one fastening component engages the attachment surface, and the inner surface of the first front side panel faces the inner surface of the first back side panel;
wherein the attachment surface is located on the inner surface and the outer surface of one of the front side panels and the back side panels.

* * * * *